(12) United States Patent
Swager et al.

(10) Patent No.: US 8,283,423 B2
(45) Date of Patent: Oct. 9, 2012

(54) POLYMER SYNTHETIC TECHNIQUE

(75) Inventors: Timothy M. Swager, Newton, MA (US); John P. Amara, Charlestown, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 84 days.

(21) Appl. No.: 12/311,378

(22) PCT Filed: Sep. 28, 2007

(86) PCT No.: PCT/US2007/020992
§ 371 (c)(1),
(2), (4) Date: Nov. 4, 2009

(87) PCT Pub. No.: WO2008/042289
PCT Pub. Date: Apr. 10, 2008

(65) Prior Publication Data
US 2010/0063225 A1    Mar. 11, 2010

Related U.S. Application Data

(60) Provisional application No. 60/848,447, filed on Sep. 29, 2006.

(51) Int. Cl.
C08F 2/00 (2006.01)
C08F 279/00 (2006.01)
C08F 38/00 (2006.01)

(52) U.S. Cl. ......... 526/75; 526/284; 526/285; 525/245; 525/326.1; 525/328.1; 525/359.3; 525/417

(58) Field of Classification Search .............. 526/75, 526/284, 285; 525/245, 328.1, 326.1, 359.3, 525/417, 938
See application file for complete search history.

(56) References Cited

U.S. PATENT DOCUMENTS

| | | |
|---|---|---|
| 3,242,186 A | 3/1966 | Dershowitz |
| 3,785,813 A | 1/1974 | Rickter |
| 4,049,616 A * | 9/1977 | Scott et al. ................ 524/532 |
| 4,356,429 A | 10/1982 | Tang |
| 4,513,078 A | 4/1985 | Sandrik et al. |
| 4,539,507 A | 9/1985 | VanSlyke et al. |
| 4,687,732 A | 8/1987 | Ward et al. |
| 4,839,112 A | 6/1989 | Wynne et al. |
| 4,841,099 A | 6/1989 | Epstein et al. |
| 4,868,103 A | 9/1989 | Stavrianopoulos et al. |
| 4,883,608 A | 11/1989 | Trujillo et al. |
| 4,894,443 A | 1/1990 | Greenfield et al. |
| 4,927,768 A | 5/1990 | Coughlin et al. |
| 4,946,890 A | 8/1990 | Meador |
| 4,957,615 A | 9/1990 | Ushizawa et al. |
| 4,992,244 A | 2/1991 | Grate |
| 4,992,302 A | 2/1991 | Lindmayer |
| 5,091,502 A | 2/1992 | Narang et al. |
| 5,155,149 A | 10/1992 | Atwater et al. |
| 5,157,261 A | 10/1992 | Grey et al. |
| 5,194,393 A | 3/1993 | Hugl et al. |
| 5,217,715 A | 6/1993 | Krivan et al. |
| 5,236,808 A | 8/1993 | Smothers |
| 5,237,582 A | 8/1993 | Moses |
| 5,244,813 A | 9/1993 | Walt et al. |
| 5,250,439 A | 10/1993 | Musho et al. |
| 5,254,633 A | 10/1993 | Han et al. |
| 5,312,896 A | 5/1994 | Bhardwaj et al. |
| 5,323,309 A | 6/1994 | Taylor et al. |
| 5,364,797 A | 11/1994 | Olson et al. |
| 5,387,462 A | 2/1995 | Debe |
| 5,414,069 A | 5/1995 | Cumming et al. |
| 5,451,663 A | 9/1995 | Kang et al. |
| 5,451,683 A | 9/1995 | Barrett et al. |
| 5,493,017 A | 2/1996 | Therien et al. |
| 5,511,547 A | 4/1996 | Markle et al. |
| 5,512,490 A | 4/1996 | Walt et al. |
| 5,512,635 A * | 4/1996 | Nubel et al. ................ 525/247 |
| 5,532,129 A | 7/1996 | Heller |
| 5,540,999 A | 7/1996 | Yamamoto et al. |
| 5,546,889 A | 8/1996 | Wakita et al. |
| 5,549,851 A | 8/1996 | Fukushima et al. |
| 5,554,747 A | 9/1996 | Sharma et al. |
| 5,556,524 A | 9/1996 | Albers |
| 5,563,056 A | 10/1996 | Swan et al. |
| 5,565,322 A | 10/1996 | Heller |
| 5,580,527 A | 12/1996 | Bell et al. |
| 5,585,646 A | 12/1996 | Kossovsky et al. |
| 5,591,787 A | 1/1997 | Schlennert et al. |
| 5,597,890 A | 1/1997 | Jenekhe |
| 5,607,864 A | 3/1997 | Ricchiero et al. |
| 5,629,353 A | 5/1997 | Steckle, Jr. et al. |
| 5,674,751 A | 10/1997 | Jaduszliwer et al. |

(Continued)

FOREIGN PATENT DOCUMENTS

DE    4121138 A1    1/1993

(Continued)

OTHER PUBLICATIONS

European Search Report for EP 02024311.9 mailed Jan. 3, 2003.
International Search Report and Written Opinion mailed Feb. 23, 2006, PCT/US2005/033261.
International Preliminary Report on Patentability for PCT/US2005/033261 mailed Mar. 29, 2007.
Invitation to Pay Additional Fees for PCT/US2006/045390 mailed Jun. 12, 2007.
International Search Report and Written Opinion for PCT/US2006/045390 mailed Sep. 24, 2007.
International Preliminary Report on Patentability for PCT/US2006/045390 mailed Jun. 5, 2008.

(Continued)

*Primary Examiner* — Fred M Teskin
(74) *Attorney, Agent, or Firm* — Wolf, Greenfield & Sacks, P.C.

(57) ABSTRACT

The present invention generally relates to methods for the synthesis of species including monomers and polymers. Methods of the invention comprise the use of chemical techniques including metathesis chemistry to synthesize, for example, monomers and/or polymers with desired functional groups.

45 Claims, 6 Drawing Sheets

U.S. PATENT DOCUMENTS

| | | | |
|---|---|---|---|
| 5,675,001 | A | 10/1997 | Hoffman et al. |
| 5,679,773 | A | 10/1997 | Holmes |
| 5,700,696 | A | 12/1997 | Chandross et al. |
| 5,705,348 | A | 1/1998 | Meade et al. |
| 5,709,994 | A | 1/1998 | Pease et al. |
| 5,710,187 | A | 1/1998 | Steckle, Jr. et al. |
| 5,710,197 | A | 1/1998 | Fischer et al. |
| 5,723,218 | A | 3/1998 | Haugland et al. |
| 5,858,907 | A | 1/1999 | Wang et al. |
| 5,869,592 | A | 2/1999 | Gagne et al. |
| 5,925,517 | A | 7/1999 | Tyagi et al. |
| 5,942,638 | A * | 8/1999 | Lichtenhan et al. .......... 556/460 |
| 5,998,204 | A | 12/1999 | Tsien et al. |
| 6,020,426 | A | 2/2000 | Yamaguchi et al. |
| 6,124,421 | A | 9/2000 | Lau et al. |
| 6,254,829 | B1 | 7/2001 | Hartmann et al. |
| 6,259,277 | B1 | 7/2001 | Tour et al. |
| 6,303,733 | B1 | 10/2001 | Lau et al. |
| 6,323,309 | B1 | 11/2001 | Swager et al. |
| 6,328,932 | B1 | 12/2001 | Carter et al. |
| 6,444,476 | B1 | 9/2002 | Morgan |
| 6,444,479 | B1 | 9/2002 | Choi |
| 6,469,123 | B1 | 10/2002 | Lau et al. |
| 6,509,110 | B1 | 1/2003 | Salbeck et al. |
| 6,556,335 | B2 | 4/2003 | Lee et al. |
| 6,589,731 | B1 | 7/2003 | Chen et al. |
| 6,605,693 | B1 | 8/2003 | Becker et al. |
| 6,610,848 | B1 | 8/2003 | Pilato et al. |
| 6,660,820 | B1 | 12/2003 | Martin et al. |
| 6,670,645 | B2 | 12/2003 | Grushin et al. |
| 6,713,298 | B2 | 3/2004 | McDevitt et al. |
| 6,743,640 | B2 | 6/2004 | Whitten et al. |
| 6,770,220 | B1 | 8/2004 | Klimant |
| 6,783,814 | B2 | 8/2004 | Swager et al. |
| 6,828,450 | B2 | 12/2004 | Hua et al. |
| 6,830,828 | B2 | 12/2004 | Thompson et al. |
| 6,835,835 | B1 | 12/2004 | Huo |
| 6,902,830 | B2 | 6/2005 | Thompson et al. |
| 6,919,139 | B2 | 7/2005 | Grushin et al. |
| 6,946,688 | B2 | 9/2005 | Grushin et al. |
| 6,962,757 | B2 | 11/2005 | Epstein et al. |
| 7,001,536 | B2 | 2/2006 | Thompson et al. |
| 7,029,765 | B2 | 4/2006 | Kwong et al. |
| 7,041,910 | B2 | 5/2006 | Swager et al. |
| 7,075,102 | B2 | 7/2006 | Grushin et al. |
| 7,078,725 | B2 | 7/2006 | Grushin et al. |
| 7,087,321 | B2 | 8/2006 | Kwong et al. |
| 7,088,757 | B1 | 8/2006 | Yu et al. |
| 7,098,060 | B2 | 8/2006 | Yu et al. |
| 7,122,383 | B2 | 10/2006 | Jones et al. |
| 7,129,518 | B2 | 10/2006 | Grushin et al. |
| 7,186,355 | B2 | 3/2007 | Swager |
| 7,208,122 | B2 | 4/2007 | Swager et al. |
| 7,250,519 | B2 | 7/2007 | Stossel et al. |
| 7,291,503 | B2 | 11/2007 | Swager |
| 7,393,503 | B2 | 7/2008 | Swager et al. |
| 7,417,146 | B2 | 8/2008 | Huo |
| 7,462,325 | B2 | 12/2008 | Hancock et al. |
| 7,521,232 | B2 | 4/2009 | Moon |
| 7,662,309 | B2 | 2/2010 | Swager et al. |
| 7,671,166 | B2 | 3/2010 | Swager et al. |
| 7,759,127 | B2 | 7/2010 | Rose et al. |
| 7,943,062 | B2 | 5/2011 | Swager et al. |
| 8,158,437 | B2 | 4/2012 | Swager et al. |
| 2002/0040805 | A1 | 4/2002 | Swager |
| 2002/0051985 | A1 | 5/2002 | Whitten et al. |
| 2002/0076830 | A1 | 6/2002 | Mauze et al. |
| 2002/0137978 | A1 * | 9/2002 | Grubbs et al. ................ 585/507 |
| 2002/0150697 | A1 | 10/2002 | Swager et al. |
| 2002/0150759 | A1 | 10/2002 | Jones et al. |
| 2002/0177136 | A1 | 11/2002 | McBranch et al. |
| 2003/0054413 | A1 | 3/2003 | Kumaraswamy et al. |
| 2003/0096138 | A1 | 5/2003 | Lecloux et al. |
| 2003/0134959 | A1 | 7/2003 | Hancock et al. |
| 2003/0178607 | A1 | 9/2003 | Swager et al. |
| 2004/0043251 | A1 | 3/2004 | Epstein et al. |
| 2004/0089867 | A1 | 5/2004 | Grushin et al. |
| 2004/0094768 | A1 | 5/2004 | Yu et al. |
| 2004/0094769 | A1 | 5/2004 | Grushin et al. |
| 2004/0106741 | A1 | 6/2004 | Kriesel et al. |
| 2004/0116650 | A1 | 6/2004 | Swager et al. |
| 2004/0121337 | A1 | 6/2004 | Deans et al. |
| 2004/0170775 | A1 | 9/2004 | Swager et al. |
| 2004/0175768 | A1 | 9/2004 | Kushon et al. |
| 2004/0188673 | A1 | 9/2004 | Grushin et al. |
| 2004/0197602 | A1 | 10/2004 | Dobbs et al. |
| 2004/0235184 | A1 | 11/2004 | Swager |
| 2004/0241768 | A1 | 12/2004 | Whitten et al. |
| 2004/0254388 | A1 | 12/2004 | Spreitzer et al. |
| 2005/0014160 | A1 | 1/2005 | Kumaraswamy et al. |
| 2005/0037232 | A1 | 2/2005 | Tyan et al. |
| 2005/0054854 | A1 | 3/2005 | Stossel et al. |
| 2005/0059168 | A1 | 3/2005 | Bazan et al. |
| 2005/0147534 | A1 | 7/2005 | Swager et al. |
| 2005/0157261 | A1 | 7/2005 | Hanebuchi et al. |
| 2005/0176624 | A1 | 8/2005 | Thompson et al. |
| 2005/0186447 | A1 | 8/2005 | Grushin et al. |
| 2005/0196775 | A1 | 9/2005 | Swager et al. |
| 2005/0220714 | A1 | 10/2005 | Kauzlarich et al. |
| 2005/0226775 | A1 | 10/2005 | Aker et al. |
| 2005/0263758 | A1 | 12/2005 | Treacher et al. |
| 2005/0285517 | A1 | 12/2005 | Yu et al. |
| 2006/0024707 | A1 | 2/2006 | Deans et al. |
| 2006/0029829 | A1 | 2/2006 | Thompson et al. |
| 2006/0057425 | A1 | 3/2006 | Grushin et al. |
| 2006/0058524 | A1 | 3/2006 | Falcou et al. |
| 2006/0073607 | A1 | 4/2006 | Rose et al. |
| 2006/0120917 | A1 | 6/2006 | Swager et al. |
| 2006/0127929 | A1 | 6/2006 | Swager et al. |
| 2006/0135772 | A1 | 6/2006 | Huo |
| 2006/0173145 | A1 * | 8/2006 | Pawlow et al. ................ 526/171 |
| 2006/0270846 | A1 | 11/2006 | Karpishin et al. |
| 2007/0081921 | A1 | 4/2007 | Swager et al. |
| 2007/0083066 | A1 * | 4/2007 | Bohm et al. ................... 568/345 |
| 2008/0085566 | A1 | 4/2008 | Swager et al. |
| 2009/0215189 | A1 | 8/2009 | Swager et al. |
| 2010/0112715 | A1 | 5/2010 | Swager et al. |
| 2010/0168352 | A1 * | 7/2010 | Arriola et al. ................. 526/171 |
| 2010/0213451 | A1 | 8/2010 | Swager et al. |
| 2010/0310424 | A1 | 12/2010 | Rose et al. |
| 2011/0142717 | A1 | 6/2011 | Swager et al. |
| 2011/0175035 | A1 | 7/2011 | Swager et al. |

FOREIGN PATENT DOCUMENTS

| | | |
|---|---|---|
| DE | 197 44 792 A1 | 4/1999 |
| DE | 198 06 037 A1 | 8/1999 |
| EP | 0 259 951 A2 | 3/1988 |
| EP | 0 442 123 A1 | 8/1991 |
| EP | 0 581 058 A1 | 2/1994 |
| EP | 0 748 805 A1 | 12/1996 |
| EP | 1 011 154 A1 | 6/2000 |
| JP | 06-322078 A | 11/1994 |
| WO | WO-89/00593 A1 | 1/1989 |
| WO | WO-95/16681 A1 | 6/1995 |
| WO | WO-98/05693 A1 | 2/1998 |
| WO | WO-99/19419 A1 | 4/1999 |
| WO | WO-99/57222 A1 | 11/1999 |
| WO | WO-00/05774 A1 | 2/2000 |
| WO | WO-00/53655 A1 | 9/2000 |
| WO | WO-01/57140 A1 | 8/2001 |
| WO | WO-02/16463 A2 | 2/2002 |
| WO | WO-02/074997 A1 | 9/2002 |
| WO | WO-02/079268 A2 | 10/2002 |
| WO | WO-03/048226 A2 | 6/2003 |
| WO | WO-2004/057014 A2 | 7/2004 |
| WO | WO-2005/030681 A1 | 4/2005 |
| WO | WO-2005/086617 A2 | 9/2005 |
| WO | WO-2006/081345 A1 | 8/2006 |
| WO | WO-2006/085319 A2 | 8/2006 |
| WO | WO-2008/019086 A2 | 2/2008 |
| WO | WO-2008/039529 A1 | 4/2008 |
| WO | WO-2008/042289 A2 | 4/2008 |
| WO | WO-2008/136805 A2 | 11/2008 |

OTHER PUBLICATIONS

Invitation to Pay Additional Fee for PCT/US2007/017380 mailed Jan. 4, 2008.

International Search Report and Written Opinion mailed Apr. 8, 2008 in PCT/US2007/017380.

International Preliminary Report on Patentability mailed Nov. 10, 2008 in PCT/US2007/017380.

International Search Report and Written Opinion mailed Dec. 14, 2007 in PCT/US2007/020961.

International Preliminary Report on Patentability dated Mar. 31, 2009, mailed Apr. 9, 2009, in PCT/US2007/020961.

Invitation to Pay Additional Fee for PCT/US2007/020992 mailed Feb. 8, 2008.

International Search Report and Written Opinion for PCT/US2007/020992 mailed Apr. 4, 2008.

International Preliminary Report on Patentability for PCT/US2007/020992 mailed Apr. 9, 2009.

International Search Report and Written Opinion mailed Oct. 27, 2008 in PCT/US2007/022670.

International Preliminary Report on Patentability dated Apr. 28, 2009, mailed May 7, 2009, in PCT/US2007/022670.

Invitation to Pay Additional Fee for PCT/US2007/021370 mailed Feb. 22, 2008.

International Search Report and Written Opinion mailed Jun. 13, 2008 in PCT/US2007/021370.

International Preliminary Report on Patentability for PCT/US2007/021370 mailed Apr. 16, 2009.

[No Author Listed] Chemical Structure for Biphenylene. CAS No. 259-79-0. Downloaded Dec. 12, 2005.

[No Author Listed] Institute for Soldier Nanotechnologies. Downloaded from http://web.mit.edu/isn/industryday/index.html on Jan. 30, 2003.

Abraham et al., "Hydrogen bonding. Part 29. Characterization of 14 Sorbent Coatings for Chemical Microsensors using a New Solvation Equation," J. Chem. Soc. Perkin Trans. 1995, 2, 369-378.

Achyuthan, KE, et al., "Fluorescence superquenching of conjugated polyelectrolytes: applications for biosensing and drug discovery", Journal of Materials Chemistry, vol. 15 (27-28): 2648-2656, (2005).

Albert et al., Designing optical sensor arrays with enhanced sensitivity for explosives detection. Proceeedings of the SPIE—The International Society for Optical Engineering. Orlando, Florida. Apr. 13-17, 1998; 3392(1-2):426-431. Abstract Only.

Amara et al., "Synthesis and Properties of Poly(phenylene ethynylene)s with Pendant Hexafluoro-2-propanol Groups," Macromolecules 2005, 38, 9091-9094.

Amara, J. et al., "Incorporation of Internal Free Volume: Synthesis and Characterization of Iptycene-Elaborated Poly(butadiene)s," Macromolecules 2004, 37, 3068-3070.

Arias-Marin et al., Amphiphilic Phenyl-Ethynylene Polymers and Copolymers. Synthesis, Characterization, and Optical Emission Properties. Macromolecules. 2003; 36:3570-3579.

Armengaud et al., "Electrochemistray of conducting polypyrrole films containing cobalt porphyrin," J. Electroanal. Chem., 1990, 277:197-211.

Audebert et al., "Description of New Redox and Conducting Polymers Based on Copper Containing Units; Emphasis on the Role of Copper in the Electron Transfer Mechanism," Synthetic Metals, 1991, 3049-3052.

Audebert et al., "Redox and Conducting Polymers Based on Salen-Type Metal Units; Electrochemical Study and Some Characteristics," New Journal of Chemistry, 1992 16(6):697-703.

Audebert et al., "Synthesis and Characteristics of New Redox Polymers Based on Copper Containing Units; Evidence for the Participation of Copper in the Electron Transfer Mechanism," New Journal of Chemistry, 1991, 15(4):235-237.

Baldo et al., "Excitonic singlet-triplet ratio in a seminconducting organic thin film," Phys. Rev. B., 1999, 60(20), 14422-14428.

Baldo et al., "High-efficiency fluorescent organic light-emitting devices using a phosphorescent sensitizer," Nature, 2000, 403, 750-753.

Barigelletti et al., "Temperature Dependence of the Luminescence of Cyclometalated Palladium(II), Rhodium(III), Platinum(II), and Platinum(IV) Complexes," Inorg. Chem. 1988, 27, 3644-3647.

Bedioui et al., "Electrochemistry of conducting polypyrrole films containing cobalt porphyrin, Part 2. New Developments and inclusion of metallic aggregates in the coordination polymer," J. Electroanal. Chem., 1991, 297:257-269.

Bedioui et al., "Electrooxidative polymerization of cobalt, nickel and manganese salen complexes in acetonitrile solution," J. Electroanal. Chem., 1991, 301:267-274.

Bedioui et al., "Poly(Pyrrole-Manganese Tetraphenylporphyrin) film Electrodes in Acetonitrile Solution," J. Electroanal. Chem., 1988, 239:433-439.

Bergstedt, T, et al., "Superquenching of fluorescent polyelectrolytes and applications for chemical and biological sensing," in Organic Photonic Materials and Devices III, Bernard Kippelen, Donal D. C. Bradley, Editors, Proceedings of SPIE vol. 4279, 94-100 (2001).

Bettelheim et al., "Electrochemical Polymerization of Amino-, Pyrrole-, and Hydroxy-Substituted Tetraphenylporphyrins," Inorganic Chemistry, 1987, 26(7):1009-1017.

Bowyer et al., Electrochemical reduction of vicinal dinitro compounds. J Org Chem. 1988; 53(22):5234-5239.

Brabec, Christoph, et al. "Plastic Solar Cells", Adv. Funct. Mater, 2001, vol. 11, No. 1, pp. 15-26.

Bredas et al., "Electronic Structure of Poly(paraphenylene vinylene): Influence of Copolymerization and Derivatization on Light-Emitting Characteristics," Am. Chem. Scoc., Div. Polym. Chem., 1994, 35, 185-186.

Brooks et al., "Synthesis and Characterization of Phosophorescent Cyclometalated Platinum Complexes," Inorg. Chem., 2002, 41(12), 3055-3066.

Brown et al., "Core-referenced ratiometric fluorescent potassium ion sensors using self-assembled ultrathin films on europium nanoparticles," IEEE Sensors Journal, 2005, 5(6), 1197-1205.

Brown et al., Fluorescence-enhancement sensing of ammonia and hydrazines via disruption of the internal hydrogen bond in a carbazolopyridinophane. Sensors Actuators B. 2005; 110:8-12.

Bustin, Absolute quantification of mRNA using real-time reverse transcription polymerase chain reaction assays. J Mol Endocrinol. Oct. 2000; 25(2):169-193.

Cabarcos et al., "Effect of the Molecular Weight and the Ionic Strength on the Photoluminescence Quenching of Water-Soluble Conjugated Polymer Sodium Poly[2-(3-thienyl)ethyloxy-4-butylsulfonate]," Macromolecules, 2005, 38(25), 10537-10541.

Cameron et al., "A conjugated polymer/redox polymer hybrid with electronic communication between metal centres," Chem. Commun., 1997, 303-304.

Carrabba et al., Hydrogen bonding in the lowest singlet n-pi-star excited state of pyrimidine. J Phys Chem. 1985; 89:674-677.

Chassot et al., "cis-Bis(2-phenylpyridine platinum(II)(CBPPP): A Simple Molecular Platinum Compound," Inorg. Chem., 1984, 23(25), 4249-4253.

Chassot et al., "Cyclometalated Complexes of Platinum(II): Homoleptic Compounds with Aromatic C,N Ligands," Inorg. Chem., 1987, 26(17), 2814-2818.

Chassot et al., "Photochemical Preparation of Luminsecent Platinum(IV) Complexes via Oxidative Addition on Luminescent Platinum(II) Complexes," J. Am. Chem. Soc., 1986, 108, 6084-6085.

Chatterjee et al.,Synthesis of Functionalized Olefins by Cross and Ring-Closing Metatheses. J Am Chem Soc. 2000; 122(15):3783-3784.

Chen, L., et al., "Surfactant-Induced Modification of Quenching of Conjugated Polymer Fluorescence by Electron Acceptors: Applications for Chemical Sensing," Chem. Phys. Lett. 330 (1-2) (2000) pp. 27-33.

Chen, Liaohai et al., "Tuning the properties of conjugated polyelectrolytes through surfactant complexation," J. Am. Chem. Soc., 2000, vol. 122 No. 38, pp. 9302-9303.

Chen, Liaohai, et al., "Highly sensitive biological and chemical sensors based on reversible fluoresence quenching in a conjugated polymer," PNAS, Oct. 26, 1999, vol. 96 No. 22, 12287-12292.

Choi et al, Oxygen-sensitive reverse-phase optode membrane using silica gel-absorbed ruthenium(II) complex embedded in gelatin film. Anal. Chim. Acta 1999, 387, 197-205.

Costa-Fernandez et al., "Sol-gel immobilized room-temperature phosphorescent metal-chelate as luminescent oxygen sensing material," *Anal. Chim. Acta.*, 1998, 360, 17-26.

Cotts, Patricia M., et al., "Equilibrium Flexibility of a Rigid Linear Conjugated Polymer," Macromolecules, 1996, vol. 29, pp. 7323-7328.

Cumming et al., "Using Novel Fluorescent Polymers as Sensory Materials for Above-Ground Sensing of Chemical Signature Compounds Emanating from Buried Landmines," IEEE Transactions on Geoscience and Remote Sensing, 2001, 39:1119-1128.

Dagani, Ron, "A Better Sensor for Nerve Gas," C&EN, Mar. 10, 2003, p. 12.

Dahm et al., "Catalytic Reduction of Iodoethane and 2-Iodopropane at Carbon Electrodes Coated with Anodically Polymerized Films of Nickel(II) Salen," Analytical Chemistry, 1994, 66(19):3117-3123.

Dai et al., Sensors and sensor arrays based on conjugated polymers and carbon nanotubes. Pure Appl Chem. 2002; 74(9):1753-1772.

Davey et al., New Rigid Backbone Conjugated Organic Polymers with Large Fluorescence Quantum Yields. J Chem Soc Chem Commun. 1995; 1433-1434.

Deans, Robert, et al., "A Poly(p-phenyleneethynylene) with a Highly Emissive Aggregated Phase", J. Am. Chem. Soc., 2000, vol. 122, pp. 8565-8566.

Decher, "Fuzzy Nanoassemblies: Toward Layered Polymeric Multicomposites," Science, 1997, 277(5330), 1232-1237.

Demchenko et al., "The problem of self-calibration of fluorescence signal in microscale sensor systems," Lab on a Chip, 2005, 5, 1210-1223.

Deng et al., "Direct Observation of the "Pac-Man" Effect from Dibenzofuran-Bridged Cofacial Bisporphyrins," J. Am. Chem. Soc. 2000, 122, 410-411.

Dijkstra et al., "Shape-Persistent Nanosize Organometallic Complexes: Synthesis and Application in a Nanofiltration Membrane Reactor," J. Org. Chem., 2003, vol. 68, No. 3, pp. 675-685.

Disney, M.D. et al., "Detection of Bacteria with Carbohydrate-Containing Fluorescent Polymers," J. Am. Chem. Soc. 2004, 126, 13343-13346.

Dougherty et al., "Photodynamic Therapy," J. Natl. Cancer Inst., 1998, 90(12), 889-905.

Dudek et al., Synthesis and energy-transfer properties of hydrogen-bonded oligofluorenes. J Am Chem Soc. Aug. 24, 2005; 127(33):11763-11768.

Dwight et al., "Perturbation of Fluorescence by Nonspecific Interactions between Anionic Poly(phenylenevinylene)s and Proteins: Implications for Biosensors," J. Am. Chem. Soc., 2004, 126(51), 16850-16859.

Ellis et al., Conductive Polymer Films as Ultrasensitive Chemical Sensors for Hydrazine and Monomethylhydrazine Vapor. Anal Chem. 1996; 68:817-822.

Erdogan et al., Synthesis and mesoscopic order of a sugar-coated poly(p-phenyleneethynylene). Macromolecules. 2002; 35:7863-7864.

Ewing et al., Detection of volatile vapors emitted from explosives with a handheld ion mobility spectrometer. Field Anal Chem Technol. 2001; 5:215-221.

Famulok et al., Nucleic acid aptamers-from selection in vitro to applications in vivo. Acc Chem Res. Sep. 2000; 33(9):591-599.

Fan, C, et al., "High-Efficiency Fluorescence Quenching of Conjugated Polymers by Proteins," J. Am. Chem Soc., 2002, 124(20): pp. 5642-5643.

Fan, C, et al., "Photoluminescence Quenchers of Water Soluble Conjugated Polymers by Viologen Derivatives: Effect of Hydrophobicity," Langmuir, 2003, 19(8): pp. 3554-3556.

Fan, C, S., et al, "Beyond superquenching: Hyper-efficient energy transfer from conjugated polymers to gold nanoparticles," PNAS, 2003, 100(11): pp. 6297-6301.

Fiesel, Rainer, et al., "A chiral poly(para-phenyleneethynylene) (PPE) derivative," Macromol. Rapid Commun., 1998, vol. 19, No. 8, pp. 427-431.

Fiesel, Rainer, et al., "Aggregation-induced CD effects in chiral poly(2,5-dialkoxy-1,4-phenylene)s," Acta Polym., 1998, vol. 49, pp. 445-449.

Fiesel, Rainer, et al., "On the Solid State Aggregation of Chiral Substituted Poly(para-phenylene)s (PPPs)," Synthetic Metals, 1999, vol. 102, pp. 1457-1458.

Fu, Dian-Kui, et al., "Alternating Poly(PyridylVinylenePhenyleneVinylene)s: Synthesis and Solid State Organizations," Tetrahedron, 1997, vol. 53, No. 45, pp. 15487-15494.

Funhoff et al., Cationic polymethacrylates with covalently linked membrane destabilizing peptides as gene delivery vectors. J Control Release. Jan. 3, 2005; 101(1-3):233-246.

Garner, C., et al., "Challenges for dielectric materials in future integrated circuit technologies," Microelectronics Reliability 2005, 45, 919-924.

Gaylord, B.S, et al., "DNA Hybridization Detection with Water-Soluble Conjugated Polymers and Chromophore-Labeled Single Stranded DNA," J. Am. Chem Soc., 2003, 125(4): pp. 896-900.

Gaylord, B.S., et al., "SNP detection using peptide nucleic acid probes and conjugated polymers: Applications in neurodegenerative disease identification," PNAS, vol. 102, No. 1, pp. 34-39 (2005).

Gaylord, B.S., et al., "Water-Soluble Conjugated Oligomers: Effect of Chain Length and Aggregation on Photoluminescence-Quenching Efficiencies," J. Am. Chem. Soc. 2001, 123(26): 6417-6418.

Gaylord, Brent S., et al., "DNA detection using water-soluble conjugated polymers and peptide nucleic acid probes," PNAS, Aug. 20, 2002, vol. 99, No. 17, pp. 10954-10957.

Gianini et al., "Chiral Cyclometalated Platinum(II) Complexes with Derivatives of Thienylpyridine as Ligands: Helical Distortion of the Square Planar (SP-4) Geometry," Inorg. Chem, 1997, 36(26), 6094-6098.

Gianini et al., "Square Planar (SP-4) and Octahedral (OC-6) Complexes of Platinum (II) and—(IV) with Predetermined Chirality at the Metal Center," Inorg. Chem., 1996, 35(17), 4889-4895.

Goldfinger et al., "Fused polycyclic aromatics via electrophile-induced cyclization reactions: application to the synthesis of graphite ribbons", J. Am. Chem. Soc., 1994, vol. 116, pp. 7895-7896.

Goldsby et al., "Oxidation of Nickel(II) Bis(salicylaldimine) Complexes: Solvent Control of the Ultimate Redox Site," Polyhedron, 1989, 8(1):113-115.

Goldsby et al., "Symmetric and Unsymmetric Nickel(II) Schiff Base Complexes; Metal-Localized Versus Ligand-Localized Oxidation," J. Coord. Chem., 1988, 19:83-90.

Grate et al., "Hydrogen Bond Acidic Polymers for Surface Acoustic Wave Vapor Sensors and Arrays," Anal. Chem. 1999, 71, 1033-1040.

Grate, "Acoustic Wave Microsensor Arrays for Vapor Sensing," Chem Rev. 2000, 100, 2627-2647.

Guice et al., "Nanoscale internally referenced oxygen sensors produced from self-assembled nanofilms on fluorescent nanoparticles," Journal of Biomedical Optics, 2005, 10(6), 064031-1-064031-9.

Guimaraes et al., On the fluoresence of pyrole derviative oligomer. Mater Sci Engineer C. 2008; 28:1076-1081.

Halkyard, Carrie E., et al., "Evidence of Aggregate Formation for 2,5-Dialkylpoly (p-phenyleneethynylenes) in Solution and Thin Films," Macromolecules, Nov. 25, 1998, vol. 31, No. 25, pp. 8655-8659.

Hard et al., Fluorescence studies of a single tyrosine in a type II DNA binding protein. Biochemistry. Jan. 10, 1989 ; 28(1):396-406.

Harrison, Benjamin S., et al., "Amplified Fluorescence Quenching in a Poly(p-phenylene)-Based Cationic Polyelectrolyte," J. Am. Chem. Soc., Aug. 16, 2001, vol. 122, No. 35, pp. 8561-8562.

Havemann, R., "High-Performance Interconnects: An Integration Overview," Proceedings of the IEEE 2001, 89(5), 586-601.

Heeger, P., et al., "Making sense of polymer-based biosensors," PNAS, vol. 96, No. 22, pp. 12219-12221 (1999).

Herbich et al. "Fluorescence Quenching by Pyridine and Derivatives Induced by Intermolecular Hydrogen Bonding to Pyrrole-Containing Heteroaromatics," J. Phys. Chem. A. 2002, 106, 2158-2163.

Hill et al., "A Mechanistic Study of the Photochemically Initiated Oxidative Addition of Isopropyl Iodide to Dimethl(1,10-phenanthroline)platinum(II)," J. Am. Chem. Soc., 1985, 107(5), 1218-1225.

Höger, Sigurd, et al., "Synthesis, Aggregation, and Adsorption Phenomena of Shape-Persistent Macrocycles with Extraannular Polyalkuly Substituents," J. Am. Chem. Soc., May 22, 2001, vol. 123, No. 24, pp. 5651-5659.

Hoferkamp et al., "Surface-Midified Electrodes Based on Nickel(II) and Copper(II) Bis(salicylaldimine) Complexes," Chemistry of Materials, 1989, 1(3):348-352.

Hoffmeister et al., "Triptycene Polymers," J. Polymer Science 1969, 7, 55-72.

Horwitz et al., "Oxidative Electropolymerization of Metal Schiff-Base Complexes," Mol. Cryst. Liq. Cryst., 1988, 160:389-404.

Houk et al., "[C-H•••O] Interactions as a Control Element in Supramolecular Complexes: Experimental and Theoretical Evaluation of Receptor Affinities for the Binding of Bipyridinium-Based Guests by Catenated Hosts," J. Am. Chem. Soc., 1999, 121(7), 1999, 1479-1487.

Houser et al.. Rational materials design of sorbent coatings for explosives: applications with chemical sensors. Talanta. May 10, 2001; 54(3):469-485.

Huang et al., "Design of a Modular-Based Fluorescent Conjugated Polymer for Selective Sensing," Angew. Chem. Int. Ed., 2004, 43(42), 5635-5638.

Huang et al., Nanostructured polyaniline sensors. Chemistry. Mar 19, 2004; 10(6):1314-1319.

Jayarahjah et al., "Oxygen Diffusion and Permeability in Alkylaminothionylphosphazene Films Intended for Phosphorescence Barometry Applications," Macromolecules, 2000, 33(15), 5693-5701.

Jensen et al., Cytoplasmic delivery and nuclear targeting of synthetic macromolecules. J Control Release. Feb. 21, 2003; 87(1-3):89-105.

Jolliet et al., "Cyclometalated Complexes of Palladium(II) and Platinum(II): cis-Configured Homoleptic and Heteroleptic Compounds with Aromatic CΛN Ligands," Inorg. Chem., 1996, 35(17), 4883-4888.

Joly et al., "Highly Effective Water-Soluble Fluorescence Quenchers of Conjugated Polymer Thin Films in Aqueous Environments," Macromolecules, 2006, 39(21), 7175-7177.

Jones, R.M., et al., "Building highly sensitive dye assemblies for biosensing from molecular building blocks," PNAS USA 2001, 98(26): 14769-14772.

Jones, R.M., et al., "Superquenching and Its Applications in J-Aggregated Cyanine Polymers," Langmuir, 2001, 17, 2568-2571.

Jones, R.M., et al., "Tuning of Superquenching in Layered and Mixed Fluorescent Polyelectrolytes," J. Am. Chem. Soc. 2001, 123: 6726-6727.

Katayama et al., Vinylideneruthenium complexes in catalysis. Coord Chem Revs. 2004; 248:1703-1715.

Kim et al. "Nonspecific Interactions of a Carboxylate-Substituted PPE with Proteins. A Cautionary Tale for Biosensor Applications," Langmuir, 2005, 21(17), 7985-7989.

Kim et al., "Control of conformational and interpolymer effects in conjugated polymers," Nature, 2001, 411, 1030-1034.

Kim et al., "Directing Energy Transfer within Conjugated Polymer Thin Films," J. Am. Chem. Soc., 2001, 123(46), 11488-11489.

Kim et al., "Ion-Specific Aggregation in Conjugated Polymers: Highly Sensitive and Selective Fluorescent Ion Chemosensors," Agnew Chem. Int. Ed., 2000, 39(21), 3868-3872.

Kim et al., "Nanoscale Fibrils and Grids: Aggregated Structures from Rigid-Rod Conjugated Polymers," Macromolecules, 1999, 32 (5), 1500-1507.

Kim et al., "Structural Control in Thin Layers of Poly)P-phenyleneethynylene)s: Photophysical Studies of Langmuir and Langmuir-Blodgett Films," J. Am. Chem. Soc., 2002, 124(26), 7710-7718.

Kim et al., "Ultrafast Energy-Transfer Dynamics between Block Copolymer and π-Conjugated Polymer Chains in Blended Polymeric Systems," Chemistry of Materials, 13(8), 2666-2674, (2001).

Kim, T.-H. et al. "A Fluorescent Self-Amplifying Wavelength Responsive Sensory Polymer for Fluoride Ion," Angew. Chem. Int. Ed. 2003, 42, 4803-4806.

Köhler, Bernhard, et al., "Novel Chiral Macrocycles Containing Two Electronically Interacting Arylene Chromophores," Chem. Eur. J., 2001, vol. 7, No. 14, pp. 3000-3004.

Kraft, Arno, et al., "Electroluminescent Conjugated Polymers—Seeing Polymers in a New Light," Agnew. Chem. Int. Ed. 1998, 37, 402-428.

Kui et al., "Structures, Photoluminescence, and Reversible Vapoluminescence Properties of Neutral Platinum(II) Complexes Containing Extended p-Conjugated Cyclometalated Ligands," J. Am. Chem. Soc. 2006, 128, 8297-8309.

Kumaraswamy, S., et al., "Fluorescent-conjugated polymer superquenching facilitates highly sensitive detection of proteases," PNAS, May 18, 2004, 101(20): pp. 7511-7515.

Kushon, S.A., et al., "Detection of DNA Hybridization via Fluorescent Polymer Superquenching," Langmuir, 2002, 18(20): pp. 7245-7249.

Kushon, S.A., et al., "Detection of single nucleotide mismatches via fluorescent polymer superquenching," Langmuir, 2003, 19(20): pp. 6456-6464.

Lamansky et al., "Highly Phosphorescent Bis-Cyclometalated Iridium Complexes: Synthesis, Photophysical Characterization, and Use in Organic Light Emitting Diodes," J. Am. Chem. Soc., 2001, 123(18), 4304-4312.

Lam Ba et al., "Imine-Bridged Planar Poly(p-phenylene) Derivatives for Maximization of Extended π-Conjugation. The Common Intermediate Approach," J. Am. Chem. Soc., 1994, 116(26), 11723-11736.

Langveld, B.M.W., et al., "Circular Dichroism and Circular Polarization of Photoluminescence of Highly Ordered Poly{3,4-di[(S)-2-methylbutoxy]thiophenel}," J. Am. Chem. Soc., 1996, vol. 118, No. 20, pp. 4908-4909.

Levitsky, et al., "Rational Design of a Nile Red/Polymer Composite Film for Fluorescence Sensing of Organophosphonate Vapors Using Hydrogen Bond Acidic Polymers," Anal. Chem. 2001, 73, 3441-3448.

Levitsky, et al., "Signal Amplification in Multichromophore Luminescence-Based Sensors," J. Phys. Chem. B, 2001, 105, 8468-8473.

Levitsky, Igor A., et al., "Energy Migration in a Poly(phenylene ethynylene): Determination of Interpolymer Transport in Anisotropic Langmuir-Blodgett Films," J. Am. Chem. Soc., 1999, vol. 121, No. 7, pp. 1466-1472.

Levitsky, Igor A., et al., "Mass and Energy Transport in Conjugated Polymer Langmuir-Blodgett Films; Conductivity, Fluorescence, and UV-Vis Studies," Macromolecules, Mar. 27, 2001, vol. 34, No. 7, pp. 2315-2319.

Li et al., Water-Soluble Poly(acrylic acid) Grafted Luminescent Silicon Nanoparticles and Their Use as Fluorescent Biological Staining Labels. Nano Letters. 2004; 4(8):1463-1467.

Li, Mei, et al., "Novel Surfactant-Free Stable Colloidal Nanoparticles Made of Randomly Carboxylated Polystyrene Ionomers," Macromolecules, 1997, vol. 30, No. 7, pp. 2201-2203.

Liao et al., "Quantification of Amplified Quenching for Conjugated Polymer Microsphere Systems," Langmuir, 2007, 23(1), 112-115.

Lim et al., Transferrin-oligomers as potential carriers in anticancer drug delivery. Pharm Res. Nov. 2004; 21(11):1985-1992.

Lipkowitz et al., A protocol for determining enantioselective binding of chiral analytes on chiral chromatographic surfaces. J Am Chem Soc. 1988; 110:3446-3452.

Liu et al., "Fluorescence Quenching Mechanism of a Polyphenylene Polyelectrolyte with Other Macromolecules: Cytochrome c and Dendrimers," Langmuir, 2005, 21(5), 1687-1690.

Liu, B., et al., "Homogeneous Fluorescence-Based DNA Detection with Water-Soluble Conjugated Polymers," Chem. Matter, vol. 16, pp. 4467-4476 (2004).

Liu, B., et al., "Methods for strand-specific DNA detection with cationic conjugated polymers suitable for incorporation into DNA chips and microarrays," PNAS, vol. 102, No. 3, pp. 589-593 (2005).

Liu, B., et al., "Optimization of the Molecular Orbital Energies of Conjugated Polymers for Optical Amplification of Fluorescent Sensors," J. Am. Chem. Soc., vol. 138, pp. 1188-1196 (2006).

Liu, et al., "Effect of Chromophore-Charge Distance on the Energy Transfer Properties of Water-Soluble Conjugated Oligomers," J. Am. Chem. Soc., vol. 125, pp. 6705-6714 (2003).

Long, T. et al., "Molecular Design of Free Volume as a Route to Low-κ Dielectric Materials," J. Am. Chem. Soc. 2003, 125, 14113-14119.

Lu L., et al., "Biocidal activity of a light-absorbing fluorescent conjugated polyelectrolyte", Langmuir, vol. 21, No. 22, pp. 10154-10159, (2005).

Lu, L., et al., "Cyanine pendant polymers on nanoparticles and in solution: superquenching and sensing applications," Polymeric Materials Science and Engineering, 2002, 86: pp. 17-18.

Lu, L., et al., "Self-assembled polymers on nanoparticles: superquenching and sensing applications," Polymer Preprints (American Chemical Society, Division of Polymer Chemistry), 2002, 43: pp. 124-125.

Lu, L., et al., "Superquenching in cyanine pendant poly-L-lysine dyes: dependence on molecular weight, solvent and aggregation," Journal of the American Chemical Society, 2002, 124: pp. 483-488.

Lu, L., et al., "Surface-Enhanced Superquenching of Cyanine Dyes as J-Aggregates on Laponite Clay Nanoparticles," Langmuir, 2002, 18(20): pp. 7706-7713.

Luo, Laibin, et al., "Thermodynamic Stabilization Mechanism of Block Copolymer Vesicles," J. Am. Chem. Soc., 2001, vol. 123, No. 5, pp. 1012-1013.

Macdiarmid, Polyanaline and polypyrrole: Where are we headed? Synthetic Metals. 1997; 84:27-34.

Maestri et al., "Absorption Spectra and Luminescence Properties of Isomeric Platinum(II) and Palladium(II) Complexes Containing 1,1'-Biphenyldiyl, 2-Phenylpyridine, and 2, 2'-Bipyridine as Ligands," Helvetica Chimica Acta 1988, 71, 1053-1059.

Maex, K. et al., "Low dielectric constant materials for microelectronics," Journal of Applied Physics 2003, 93(11), 8793-8841.

Maier, G., "Low dielectric constant polymers for microelectronics," Prog. Polym. Sci. 2001, 26, 3-65.

Manes et al., Extraction-spectrophotometric determination of hydrazine with 2-hydroxy-1-naphthaldehyde. Analyst. 1987; 112:1183-1184.

Martin, et al., "Picosecond Laser Photolysis Studies of Deactivation Processes of Excited Hydrogen-Bonding Complexes. 2. Dibenxocarbazole-Pyridine Systems," J. Phys. Chem. 1982, 86, 4148-4156.

Martin, S. et al., "Development of a Low-Dielectric-Constant Polymer for the Fabrication of Integrated Circuit Interconnect," Adv. Mater. 2000, 12(23), 1769-1778.

Matloka et al., The acyclic diene metatheis (ADMET) polymerization approach to silicon containing materials. J Mol Catalysis. 2006; 257:89-98.

McGill, et al., "Choosing polymer coatings for chemical sensors," Chemtech 1994, 24, 27-37.

McQuade, D. Tyler, et al., "Conjugated Polymer-Based Chemical Sensors," Chem. Rev., 2000, vol. 100, No. 7, pp. 2537-2574.

McQuade, D. tyler, et al., "Two-Dimensional Conjugated Polymer Assemblies: Interchain Spacing for Control of Photophysics," J. Am. Chem. Soc., 2000, vol. 122, No. 24, pp. 5885-5886.

Medintz et al., "Quantum dot bioconjugates for imaging, labelling and sensing," Nature Materials, 2005, 4(6), 435-446.

Miao, Yi-Jun, et al., "Fluorescence Sensory Polymers Containing Rigid Non-planar Aromatic Scaffolds," Proceedings of the 1997 Boston meeting, vol. 39, No. 2, pp. 1081-1082, Aug. 23-27, 1998, Polym. Prepr. Div. Polym. Chem. Am. Chem. Soc.; Polymer Preprints, Division of Polymer Chemistry, American Chemical Society, Aug. 1998 ACS, Washington D.C.

Mitschke, Ullrich et al., "The electroluminescence of organic materials," J. Mater. Chem., 2000, vol. 10, pp. 1471-1507.

Miyasaka, et al., "Femtosecond-Picosecond Laser Photolysis Studies on the Mechanisms of Fluorescence Quenching Induced by Hydrogen-Bonding Interactions—1-Pyrenol-Pyridine Systems," J. Phys. Chem. 1993, 97, 8222-8228.

Moisy et al., "Epoxidation of cis-cyclooctene by Molecular Oxygen Electrocatalysed by Polypyrrole-Manganese Porphyrin Film Modified Electrodes," J. Electroanal. Chem., 1988, 250:191-199.

Moon et al., Live-cell-permeable poly(p-phenylene ethynylene). Angew Chem Int Ed Engl. 2007; 46(43):8223-8225.

Moon, Joong Ho, et al., "Capture and detection of a quencher labeled oligonucleotide by poly)phenylene ethynylene) particles," Chem. Commun., Jan. 2003, vol. 1, pp. 104-105.

Morgen, M., et al., "Low Dielectric Constant Materials for ULSI Interconnects," Annu. Rev. Mater. Sci. 2000, 30, 645-680.

Morin et al., "Syntheses of Conjugated Polymers Derived from N-Alkyl-2,7-carbazoles," Macromolecules, 2001, 34(14), 4680-4682.

Moroni et al., Rigid Rod Conjugated Polymers for Nonlinear Optics. 3. Intramolecular H Bond Effects on Poly(phenyleneethynylene) Chains. Macromolecules. 1997; 30:1964-1972.

Murarka, S., "Materials aspects of copper interconnection technology for semiconductor applications," Materials Science and Technology 2001, 17, 749-758.

Ng et al., Syntheses and characterisation of electrically conductive and fluorescent poly[3-(w-bromoalkyl)thiophenes]. Synthetic Metals. 1999; 100:269-277.

Nie et al., "Immobilization of polydiacetylene onto silica microbeads for colorimetric detection," J. Mater. Chem., 2006, 16, 546-549.

Norvez, S., et al., "Epitaxygens: mesomorphic properties of triptycene derivatives," Liquid Chemicals, 1993, vol. 14, No. 5, pp. 1389-1395.

Oda, Masao, et al., "Chiroptical properties of chiral-substituted polyfluorenes," Synthetic Metals, 2000, vol. 111-112, pp. 575-577.

Oda, Masao, et al., "Circularly Polarized Electroluminescence from Liquid-Crystalline Chiral Polyfluorenes," Advanced Materials, 2000, vol. 12, No. 5, pp. 362-365.

Office Action from U.S. Appl. No. 11/252,419 dated Mar. 13, 2008.
Office Action from U.S. Appl. No. 11/252,419 dated Dec. 12, 2008.
Office Action from U.S. Appl. No. 11/252,419 dated Jun. 12, 2009.

Okamoto, I. et al., "Orbital Unsymmetrization Affects Facial Selectivities of Diels-Alder Dienophiles," J. Org. Chem. 1996, 61, 3155-3166.

Ortege-Barrales et al., Solid-phase spectrophotometric determination of trace amounts of hydrazine at sub-ng ml-1 level. Anal Chim Acta. 1997; 353:115-122.

Orynbayeva et al., Visualization of membrane processes in living cells by surface-attached chromatic polymer patches. Angew Chem Int Ed Engl. Feb. 4, 2005; 44(7):1092-1096.

Osborne et al., Nucleic Acid Selection and the Challenge of Combinatorial Chemistry. Chem Rev. Apr. 1, 1997; 97(2):349-370.

Ow et al., "Bright and stable core-shell fluorescent silica nanoparticles," Nano Letters, 2005, 5(1), 113-117.

Park et al., "Ratiometric Optical PEBBLE Nanosensors for Real-Time Magnesium Ion Concentrations Inside Viable Cells," Anal. Chem., 2003, 75(15), 3784-3791.

Patel, et al., "Chemicapacitive microsensors for volatile organic compound detection," Sensors and Actuators B, 2003, 96, 541-553.

Peeters, Emiel, et al., "Circularly Polarized Electroluminescence from a Polymer Light-Emitting Diode," J. Am. Chem. Soc., 1997, vol. 119, No. 41, pp. 9909-9910.

Pei et al., First Hydrogen-Bonding-Induced Self-Assembled Aggregates of a Polyfluorene Derivative. Macromolecules. 2003; 36:323-327.

Pei et al., Polymer Light-Emitting Electrochemical Cells: In Situ Formation of a Light-Emitting p-n Junction. J Am Chem Soc. 1996; 118(16):3922-3929.

Peng, Kang-Yung, et al., "Efficient Light Harvesting by Sequential Energy Transfer across Aggregates in Polymers of Finite Conjugational Segments with Short Aliphatic Linkages," J. Am. Chem. Soc., 2001, vol. 123, pp. 11388-11397.

Perr et al., Solid phase microextraction ion mobility spectrometer interface for explosive and taggant detection. J Sep Sci. Feb. 2005; 28(2):177-183.

Pingarron et al., Carbon fibre microelectrodes modified with rhodium for the electrocatalytic determination of hydrazine. Anal Chim Acta. 2001; 439:281-290.

Pinnaduwage, et al., "Detection of 2,4-dinitrotoluene using microcantilever sensors," Sensors and Actuators B, 2004, 99, 223-229.

Pisaravskii et al., Fluoresence spectrum and quantum yield of DNA in solution. Zhurnal Prikladnoi Spektroskipii. 1966; 5:621-624.

Place, Ileane, et al., "Stabilization of the Aggregation of Cyanine Dyes at the Molecular and Nanoscopic Level," Langmuir, Jul. 28, 2000, vol. 16, No. 23, pp. 9042-9048.

Pschirer, Neil G., et al., "Poly(fluorenyleneethynylene)s by Alkyne Metathesis: Optical Properties and Aggregation Behavior," Macromolecules, May 9, 2000, vol. 33, No. 11, pp. 3961-3963.

Ratcliffe, Polypyrrole-based sensor for hydrazine and ammonia. Anal Chim Acta. 1990; 239:257-262.

Reddinger et al., "Electroactive π-Conjugated Polymers Based on Transition Metal-Containing Thiophenes Capable of Sensing Ionic and Neutral Species," ACS Polym. Prepr., 1997, 321-322.

Reddinger et al., "Electroactive π-Conjugated Polymers Based on Transition Metal-Containing Thiophenes," Synthetic Metals, 1997, 84:225-226.

Reddinger et al., "Tunable Redox and Optical Properties Using Transition Metal-Complexed Polythiophenes," Macromolecules, 1997, 30(3):673-675.

Rendina et al., "Oxidative Addition Reactions of Organplatinum (II) Complexes with Nitrogen-Donor Ligands," J. Chem. Rev. 1997, 1735-1754.

Rininsland, F., et al., "High-throughput kinase assays with protein substrates using fluorescent polymer superquenching," BMC Biotechnology, vol. 5, No. 16 (2005).

Rininsland, F., et al., "Metal ion-mediated polymer superquenching for highly sensitive detection of kinase and phosphatase activities," PNAS, Oct. 26, 2004, 101(43): pp. 15295-15300.

Rose et al., "Excited-State Lifetime Modulation in Triphenylene-Based Conjugated Polymers," J. Am. Chem. Soc., 2001, 123:11298-11299.

Rose et al., Sensitivity gains in chemosensing by lasing action in organic polymers. Nature. Apr. 14, 2005; 434(7035):876-879.

Sandrini et al., "Photochemistry of the Orthometalated cis-Bis[2-(2-thienyl)pyridine]platinum(II) Complex in Halocarbon Solvents," J. Am. Chem. Soc. 1987, 109, 7720-7724.

Schwarz et al., "Spectroscopic Studies of Cyclometalated Platinum(II) Complexes: Optical Absorption and Emission of Single-Crystal cis-Bis(benzo[h]quinolinato)platinum(II)," Inorg. Chem. 1989, 28, 1053-1059.

Segawa et al., "Approaches to conducting polymer devices with nano-structure: Electrochemical construction of one-dimensional and two-dimensional prophyrinoligothiophene co=polymers," Synthetic Metals, 1995, 71:2151-2154.

Shabani et al., Indirect Spectrophotometric Determination of Trace Quantities of Hydrazine. Bull Korean Chem Soc. 2004; 25:213-215.

Shamiryan, D. et al., "Low-k dielectric materials," Materials Today, Jan. 2004.

Shimidzu et al., "Approaches to conducting polymer devices with nanostructures: photoelectrochemical function of one-dimensional and two-dimensional porphyrin polymers with oligothienyl molecular wire," Journal of Photochemistry and Photobiology A: Chemistry 99, 1995, Article 4168:1-7.

Smet, M. et al., "Synthesis of the Formal Diels-Alder Adducts of N-substituted Dehydromaleimides and Anthracene," Molecules 2000, 5, 179-181.

Snow A.W., et al., "Synthesis and Evaluation of Hexafluorodimethylcarbinol Functionalized Polymers as Microsensor Coatings," Journal of Applied Polymer Science, 1991, vol. 43, pp. 1659-1671.

Swager, Timothy M., "The Molecular Wire Approach to Sensory Signal Amplification," Acc. Chem. Res., 1998, vol. 31, No. 5, pp. 201-207.

Swager, Timothy M., et al., "Fluorescence Studies of Poly(p-phenyleneethynylene)s: The Effect of Anthracene Substitution," J. Phys .Chem., 1995, vol. 99, No. 14, pp. 4886-4893.

Tan, Chunyan, et al., "Photophysics, aggregation and amplified quenching of a water-soluble poly(phenylene ethynylene)," Chem. Commun., 2002, pp. 446-447.

Thomas, III et al. "Designing Amplifying Polymer Sensors for Explosives and Toxic Chemicals," Polymeric Materials: Science and Engineering 2006, 95, 81-82.

Thomas, III et al. "Trace Hydrazine Detection with Fluorescent Conjugated Polymers: A Turn-On Sensory Mechanism," Adv. Materials 2006, 18, 1047-1050.

Thomas, III et al., " Dark-Field Oxidative Addition-Based Chemosensing: New Bis-cyclometalated Pt(II) Complexes and Phosphorescent Detection of Cyanogen Halides," J. Am. Chem. Soc. 2006, 128, 16641-16648.

Thomas, III et al., "Amplifying fluorescent polymer sensors for the explosives taggant 2,3-dimethyl-2,3-dinitrobutane (DMNB)," Chem. Commun. 2005, 4572-4574.

Thomas, III et al., "Conjugated Polymer Sensors: Design Principles Towards Enhanced Versatility," presented at the Army Science Conference, Dec. 2004.

Thomas, III et al., "Conjugated Polymer Sensors: Detection of DMNB and Hydrazine," presented at the Materials Research Symposium, Boston, MA (Dec. 2005).

Thomas, III et al., "Conjugated Polymer Sensors: Detection of DMNB and Hydrazine," presented to the American Chemical Society at the 230th National Meeting, Washington, D.C. (Aug. 28-Sep. 1, 2005).

Thomas, III et al., "Synthesis and Optical Properties of Simple Amine-Containing Conjugated Polymers," Macromolecules, 2005, 38(7), 2716-2721.

Toal et al., Polymer sensors for nitroaromatic explosives detection. J Mater Chem. 2006; 16:2871-2883.

Treichel, H. et al., "Integration Challenges for Low Dielectric Constant Materials," Advanced Engineering Materials. 2001; 7(3):461-464.

Tsai et al., New Thiophene-Linked Conjugated Poly(azomethine)s: Theoretical Electronic Structure, Synthesis, and Properties. Macromolecules. 2005; 38:1958-1966.

Van Houten, Kelly A., et al., "Rapid Luminescent Detection of Phosphate Esters in Solution and the Gas Phase Using (dppe)Pt{S2C2(2-pyridyl)(CH2CH2OH)}," J. Am. Chem. Soc., 1998, vol. 120, No. 47, pp. 12359-12360.

Vilas-Boas et al., "New Insights into the Structire and Properties of Electroactive Polymer Films Derived from [Ni(salen)]," Inorganic Chemistry, 1997, 36(22):4919-4929.

Virji et al., Hydrazine Detection by Polyaniline Using Fluorinated Alcohol Additives. Chem Mater. 2005; 17(5):1256-1260.

Virji et al., Polyaniline Nanofiber Gas Sensors: Examination of Response Mechanisms. Nano Letters. 2004; 4(3):491-496.

Von Zelewsky et al., "Thermal and Photochemical Oxidative Addition of Alkyl Halides to the Cyclometalated Complex cis-Bis[2-(2'-thienyl)pyridine]platinum(II)," Inorg. Chem. 1993, 32, 4585-4593.

Walters, Keith A., et al., "Photophysical Consequences of Conformation and Aggregation in Dilute Solutions of π-Conjugated Oligomers," Langmuir, 1999, vol. 15, pp. 5676-5680.

Waluk, "Hydrogen-Bonding-Induced Phenomena in Bifunctional Heteroazaaromatics," Acc. Chem. Res. 2003, 36, 832-838.

Wang et al., Catalytic-adsorptive stripping voltammetric measurements of hydrazines. Talanta. Dec. 1988; 35(12):965-968.

Wang et al., Hydrazine Detection Using a Tyrosinase-Based Inhibition Biosensor. Anal Chem. 1995; 67:3824-3827.

Wang, C., et al., "Biosensors from conjugated polyelectrolyte complexes," PNAS, 2002, 99(1): pp. 49-53.

Wang, D., et al. "Photoluminescence Quenching of Conjugated Macromolecules by Bipyridinium Derivatives in Aqueous Media: Charge Dependence," Langmuir, 2001, 17(4): 1262-1266.

Wang, J., et al., "Photoluminescence of Water-Soluble Conjugated Polymers: Origin of Enhanced Quenching by Charge Transfer," Macromolecules 2000, 33(14): 5153-5158.

Wang, S., et al., "Fluorescein Provides a Resonance Gate for FRET from Conjugated Polymers to DNA Intercalated Dyes," J. Am. Chem. Soc., vol. 126, pp. 5446-5451 (2004).

Weder, Christoph, et al., "Efficient Solid-State Photoluminescence in New Poly(2,5-dialkoxy-p-phenyleneethynylene)s," Macromolecules, 1996, vol. 29, No. 15, pp. 5157-5165.

Whitten, D., et al., "From Superquenching to Biodetection: Building Sensors Based on Fluorescent Polyelectrolytes" Optical Sensors and Switches, pp. 189-208 (2001).

Willis et al., Fluoresence decay kinetics of tyrosinate and tyrosine hydrogen-bonded complexes. J Physical Chemistry 1991; 95:1585-1589.

Wolfbeis, "Materials for fluorescence-based optical chemical sensors," J. Mater. Chem., 2005, 15, 2657-2669.

Wosnick et al., "Layer-by-Layer Poly(phenylene ethynylene) Films on Silica Microspheres for Enhanced Sensory Amplification," Macromolecules, 2005, 38(22), 9287-9290.

Wosnick et al., "Synthesis and Application of Poly(phenylene Ethynylene)s for Bioconjugation: A Conjugated Polymer-Based Fluorogenic Probe for Proteases," J. Am. Chem. Soc., 2005, 127(10), 3400-3405.

Wu et al., "Preparation and Encapsulation of Highly Fluorescent Conjugated Polymer Nanoparticles," Langmuir, 2006, 22(7), 2956-2960.

Wu et al., Novel water-soluble fluorescent polymer containing recognition units: Synthesis and interactions with PC12 cell. Euro Polymer J. 2005; 41:1985-1992.

Wu, Chi, et al., "Novel Nanoparticles Formed via Self-Assembly of Poly(ethylene glycol-b-sebacic anhydride) and Their Degradation in Water," Macromolecules, Oct. 31, 2000, vol. 33, No. 24, pp. 9040-9043.

Xia, et al., "A high-throughput screening assay for Kinases and Phosphatases via metal ion-mediated fluorescent polymer superquenching," American Laboratory, Oct. 2004, 36(20): pp. 15-19.

Xia, W., et al., "Applications of fluorescent polymer superquenching to high throughput screening assays for protein kinases," A&DDT, Apr. 2004, 2(2): pp. 183-192.

Yamaguchi et al., Light-emitting efficiency tuning of rod-shaped pi conjugated systems by donor and acceptor groups. J Am Chem Soc. Jul. 6, 2005; 127(26):9332-9333.

Yang et al., Growth of Ultrathin Covalently Attached Polymer Films: Uniform Thin Films for Chemical Microsensors. Langmuir. 1998; 14:1505-1507.

Yang, Jye-Shane, et al., "Anomalous crystal packing of iptycene secondary diamides leading to novel chain and channel networks," Tetrahedron Letters, Oct. 7, 2000, vol. 41, Issue 41, pp. 7911-7915.

Yang, Jye-Shane, et al., "Fluorescent Porous Polymer Films as TNT Chemosensors: Electronic and Structural Effects," J. Am. Chem. Soc., 1998, vol. 120, No. 46, pp. 11864-11873.

Yang, Jye-Shane, et al., "Porous Shape Persistent Fluorescent Polymer Films: An Approach to TNT Sensory Materials," J. Am. Chem. Soc., Jun. 3, 1998, vol. 120, No. 21, pp. 5321-5322.

Yu et al., New efficient blue light emitting polymer for light emitting diodes. Chem Commun. 1999: 1837-1838.

Yuan et al., Fiber optic chemical sensors using a modified conducting polymer cladding. SPIE. 2001; 4205:170-179.

Zahn et al., "Three-Dimensional Electronic Delocalization in Chiral Conjugated Polymers," Angew. Chem. Int. Ed. Engl., 2002, 41(22):4225-4230.

Zhang et al., Fluorescent detection of chemical warfare agents: functional group specific ratiometric chemosensors. J Am Chem Soc. Mar. 26, 2003; 125(12):3420-3421.

Zhang et al., Fluorescent Detection Of Chemical Warfare Agents: Functional Group Specific Ratiometric Chemosensors. Supporting Information. Downloaded from http://pubs.acs.org/subscribe/journals/jacsat/suppinfo/ja029265z/ja029265zsi20030125_030500.pdf.

Zhang, Guangzhao, et al., "Formation of Novel Polymeric Nanoparticles," Accounts of Chemical Research, Jan. 6, 2001, vol. 34, No. 3, pp. 249-256.

Zhao et al., "Sensory Responses in Solution vs Solid State: A Fluorescence Quenching Study of Poly(iptycenebutadiynylene)s," Macromolecules, 2005, 38(22), 9377-9384.

Zheng et al., Biotinylated poly(p-phenylene ethynylene): unexpected energy transfer results in the detection of biological analytes. Chem Commun (Camb). Dec. 21, 2004; (24):2798-2799. Epub Nov. 4, 2004.

Zheng, J., et al., "Energy Transfer from Biotinylated Poty(p-phenylene ethynylene): New Insights for Amplified Fluorescence-Based Biosensors," Chem. Commun., 2004, 2798-2799.

Zheng, J. et al., Supporting Information for "Energy Transfer from Biotinylated Poly)p-phenylene ethynylene): New Insights for Amplified Fluorescence-Based Biosensors".

Zhou et al., Novel Polyphenylenes Containing Phenol-Substituted Oxadiazole Moieties as Fluorescent Chemosensors for Fluoride Ion. Macromolecules. 2005; 38:2148-2153.

Zhou, Qin, et al. "Fluorescent Chemosensors Based on Energy Migration in Conjugated Polymers: The Molecular Wire Approach to Increased Sensitivity," J. Am. Chem. Soc., 1995, vol. 117, No. 50, pp. 12593-12602.

Zhou, Qin, et al., "Methodology for Enhancing the Sensitivity of Fluorescent Chemosensors: Energy Migration in Conjugated Polymers," J. Am. Chem. Soc., 1995, vol. 117, No. 26 pp. 7017-7018.

Zhu et al., "Conducting Polymetallorotaxanes: A Supramolecular Approach to Transition Metal Ion Sensors," Journal of the American Chemical Society, 1996, 118(36):8713-8714.

Zhu et al., "Design of Conducting Redox Polymers: A Polythiophene-Ru(bipy)3n Hybrid Material," Adv. Mater., 1996, 8(6):497-500.

Zotti et al., "Conductivity in Redox Modified Conducting Polymers. 2. Enhanced Redox Conductivity in Ferrocene-Substituted Polypyrroles and Polythiophenes," Chem. Mater., 1995 7(12):2309-2315.

* cited by examiner

POLYMER SYNTHETIC TECHNIQUE

RELATED APPLICATIONS

This application is a national stage filing under 35 U.S.C. §371 of International Application No. PCT/US2007/020992, filed Sep. 28, 2007, which claims the benefit of U.S. Provisional Application No. 60/848,447, filed Sep. 29, 2006. The contents of each of these applications are incorporated herein by reference in their entireties for all purposes.

STATEMENT REGARDING FEDERALLY SPONSORED RESEARCH OR DEVELOPMENT

This invention was made with government support under Grant Number DAAD19-02-D-0002 awarded by the Army Research Office. The government has certain rights in this invention.

FIELD OF THE INVENTION

The present invention relates to synthetic methods for species including monomers and polymers.

BACKGROUND OF THE INVENTION

Metathesis chemistry has been widely used in the synthesis of high molecular weight polymers and other materials. In the presence of transition metal-catalysts, including commercially available ruthenium-based Grubbs-type carbenes and molybdenum-based and tungsten-based Schrock alkylidenes, olefins can exchange groups around double bonds via metallocyclobutane intermediates to form new double bonds. Olefin metathesis employs carbon-carbon double bonds, which may typically be unreactive toward other reagents, as the reactive functional groups. In some cases, metathesis reactions may be performed in the presence of a wide variety of functional groups and under mild conditions, such as at room temperature.

SUMMARY OF THE INVENTION

The present invention provides methods for synthesizing a polymer containing a desired functional group, comprising providing a species comprising a carbon-carbon double bond; performing a metathesis reaction between the species and a functional group precursor to form a covalent bond therebetween, thereby forming a functionalized species; and polymerizing the functionalized species, with or without other non- or differently-functionalized species, to form a polymer comprising the functional group.

The present invention also provides methods for synthesizing a polymer containing a desired functional group, comprising providing a polymer comprising at least one carbon-carbon double bond; and performing a metathesis reaction between the polymer and a functional group precursor such that a covalent bond is formed therebetween, thereby forming a polymer comprising the functional group.

The present invention also provides methods for synthesizing a polymer containing a desired functional group, comprising providing a species comprising a carbon-carbon double bond; and performing a metathesis reaction between the species and a functional group precursor to form a covalent bond therebetween, thereby forming a functionalized species; wherein the species is a monomer, oligomer, or polymer, and wherein, when the species is a monomer or oligomer, the method further comprises polymerizing the functionalized species, with or without other non- or differently-functionalized species, to form a functionalized polymer.

DETAILED DESCRIPTION

The present invention generally relates to methods for the synthesis of species including monomers and polymers. Methods of the invention comprise the use of chemical techniques including metathesis chemistry to synthesize, for example, monomers and/or polymers with desired functional groups.

Figure 2A:
FIG. 2 shows examples of metathesis reactions including (a) cross metathesis, (b) ring-closing metathesis, and (c) ring-opening metathesis.
Figure 2B:
Figure 2C:

In some embodiments, methods of the invention employ the use of olefin metathesis chemistry. As used herein, "metathesis" or "olefin metathesis" is given its ordinary meaning in the art and refers to a chemical reaction in which two reacting species exchange partners in the presence of a transition-metal catalyst, according to the formula shown in Scheme 1, and ethylene is formed as a byproduct. FIGS. 2A-C show examples of different kinds of metathesis reactions including cross metathesis (FIG. 2A), ring-closing metathesis (FIG. 2B), and ring-opening metathesis (FIG. 2C). Other examples of metathesis reactions may include acyclic diene metathesis, alkyne metathesis, enyne metathesis, and the like.

Scheme 1

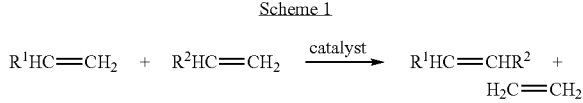

In some cases, methods of the invention employ the use of metathesis chemistry to synthesize a species having a desired functional group. As used herein, the term "species" may refer to any chemical moiety including monomers, oligomers, polymers, and the like. The method may comprise performing a metathesis reaction between a species and a functional group precursor to form a covalent bond therebetween to form a functionalized species. The method may comprise exposure of the species and the functional group precursor to a metathesis catalyst. In some cases, the metathesis catalyst may comprise ruthenium, molybdenum, or tungsten. As used herein, a "functional group precursor" refers to a chemical moiety containing a desired functional group that may be reacted to form a covalent bond between the species (e.g., monomer, oligomer, polymer) and the desired functional group. In some embodiments, the species and/or functional group precursor may comprise a carbon-carbon double bond. The carbon-carbon double bond may be ethylene, mono-substituted (e.g., alpha-olefin), di-substituted (e.g., 1,1-disubstituted, 1,2-disubstituted), tri-substituted, tetra-substituted, or the like. In some embodiments, the carbon-carbon double bond may be an alpha-olefin. For example, the species and the functional group precursor may each comprise at least one alpha-olefin wherein, upon exposure to a metathesis catalyst, a covalent bond is formed therebetween to produce a functionalized species.

Figure 1A:
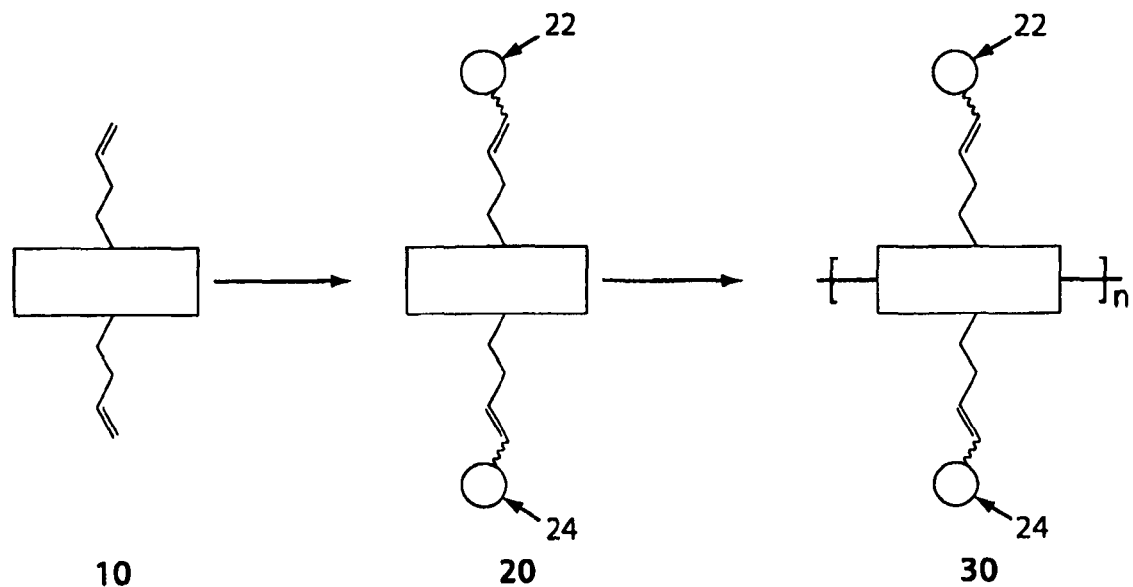
FIG. 1A shows the synthesis of a polymer, wherein the synthesis comprises functionalization of a species via metathesis chemistry, followed by polymerization of the functionalized species.
Figure 4:
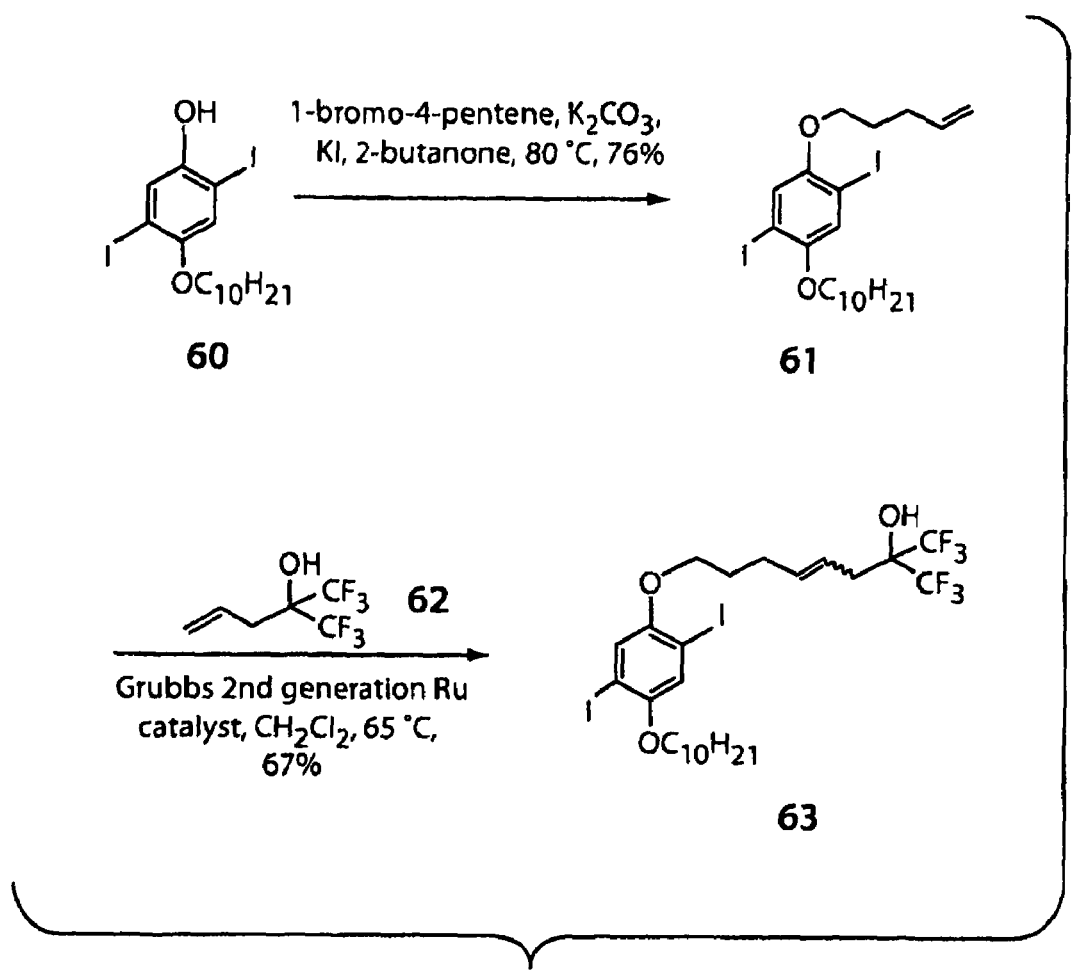
FIG. 4 shows a schematic synthesis of a monomer having a hexafluoroisopropanol group, according to one embodiment of the present invention.
Figure 5:
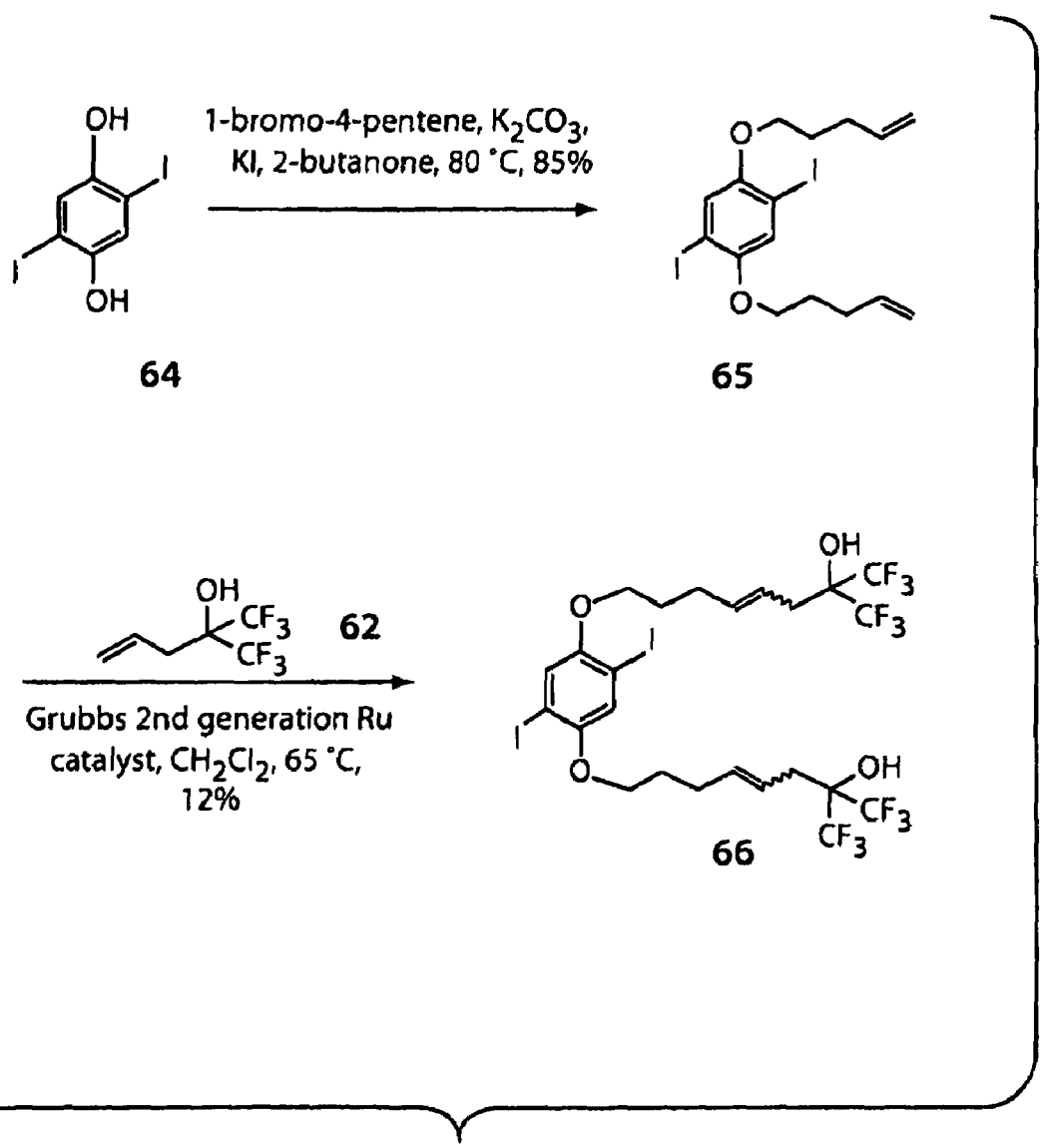
FIG. 5 shows a schematic synthesis of a monomer having two hexafluoroisopropanol groups, according to one embodiment of the present invention.

In some embodiments, the species is a monomeric species, wherein methods of the invention may comprise the synthesis of a functionalized monomer. The synthesis of functionalized monomers is described herein by way of example only, and it should be understood that other species, including oligomers, polymers, and the like, may also be suitable for use in the invention. As shown by the illustrative embodiment in FIG. 1A, monomer 10 comprises two alpha-olefins within pendant sidechains. A metathesis reaction may then be performed between monomer 10 and functional group precursor 22, which also comprises an alpha olefin, to form functionalized monomer 20, which is covalently bonded to functional groups 24 and 26. Monomer 20 may optionally be further reacted, either prior to or subsequent to the metathesis reaction, to form a desired, functionalized species. In two illustrative embodiments, FIG. 4 shows a schematic synthesis of a monomer comprising a hexafluoroisopropanol group and FIG. 5 shows a schematic synthesis of a monomer comprising two hexafluoroisopropanol groups.

Polymerization of functionalized monomer 20 may then provide polymer 30 comprising functional groups 24 and 26. (FIG. 1A) Polymerization of the functionalized monomer may be performed with or without other types of species (e.g., monomers, oligomers, polymers, and the like), including non-functionalized or differently-functionalized species. In some cases, a functionalized monomer is polymerized to form a homopolymer or a homopolymeric portion of a polymer. In some cases, the functionalized monomer is polymerized in the presence of a second, different monomer to form a copolymer (e.g., random co-polymer). It should be understood that the functionalized monomer may be polymerized with any number of additional, different monomers to produce a desired polymer. The ratio of functionalized monomer to other monomers may be selected to afford polymers having a desired amount (e.g., concentration) of functional groups within each polymer chain. The functionalized monomers may be polymerized according to known methods, including, but not limited to, cationic polymerization, anionic polymerization, radical polymerization, condensation polymerization, Wittig polymerization, ring-opening polymerization, cross-coupling polymerization, addition polymerization, chain polymerization, or the like.

In some embodiments, methods of the invention employ the use of metathesis chemistry to functionalize a polymeric species. For example, a metathesis reaction between a polymer comprising at least one carbon-carbon double bond and a functional group precursor may be performed such that a covalent bond is formed therebetween, thereby forming a polymer comprising the functional group. In some cases, the polymer may comprise a plurality of carbon-carbon double bonds. In some cases, the carbon-carbon double bonds may be positioned adjacent, within, or pendant to the polymer backbone. In some cases, the carbon-carbon double bonds may be positioned pendant to the polymer backbone, such as within a pendant side chain. For example, the polymer comprising at least one carbon-carbon double bond may comprise a pendant group comprising the carbon-carbon double bond. The carbon-carbon double bond may be ethylene, mono-substituted (e.g., alpha-olefin), di-substituted (e.g., 1,1-disubstituted, 1,2-disubstituted), tri-substituted, tetra-substituted, or the like. In some embodiments, the carbon-carbon double bond may be an alpha-olefin positioned within a pendant side chain (e.g., alkyl, heteroalkyl, or the like) of the polymer.

Some embodiments of the invention comprise the use of species (e.g., monomers, polymers) having pendant side chains comprising terminal, monosubstituted olefins. For example, the pendant side chain may be an alkenyl chain comprising one, terminal, carbon-carbon double bond. One particular advantage of such methods is that species comprising terminal carbon-carbon double bonds may be readily synthesized, as halo-alkenes of various chain lengths are commercially available.

Figure 1B:
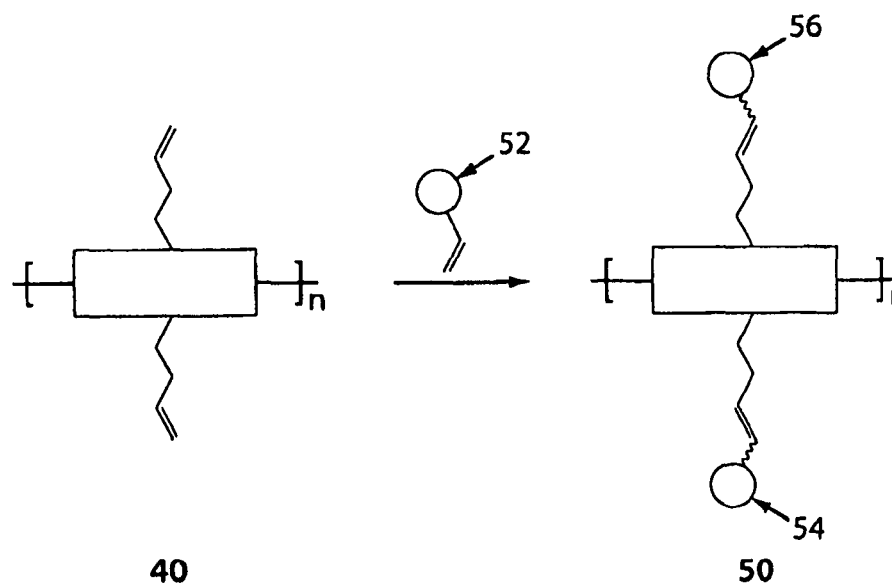
FIG. 1B show the synthesis of a polymer, wherein the synthesis comprising functionalization of a polymer via metathesis chemistry.

As shown in FIG. 1B, polymer 40 may comprise pendant side chains having terminal carbon-carbon double bonds. A metathesis reaction may then be performed between polymer 40 and functional group precursor 52, which also comprises an alpha olefin, to form functionalized polymer 50, which is covalently bonded to functional groups 54 and 56.

In some embodiments, methods of the present invention may be particularly advantageous since they may allow for the modular synthesis of various monomers, oligomers, and/or polymers. For example, a monomer and/or polymer may be synthesized comprising a plurality of pendant side chains having a terminal olefin. The terminal olefin may be functionalized via a metathesis reaction as described herein with any desired functional group selected to impart a particular property on the monomer and/or polymer. In some cases, a monomer and/or polymer may be functionalized with for example, hydrophilic groups such as a poly(ethylene glycol) groups to increase the water solubility of the monomer and/or polymer. In some cases, the polymer may be functionalized with, for example, hydrophobic groups such as alkyl groups to decrease the water solubility of the monomer and/or polymer. Other examples of properties of monomers and/or polymers that may be modulated by the addition of functional groups, include solubility, steric size, particle size, electrostatic properties, optical properties, secondary and/or tertiary structures, and the like.

In one set of embodiments, monomers and/or polymers may be designed and synthesized for determination of a target analyte, wherein the monomer or polymer may be functionalized with a binding site capable of interacting with a target analyte. For example, a sample suspected of containing an analyte may be exposed to a monomer or polymer as described herein. The analyte may interact with the monomer or polymer to cause a change in a property of the monomer or polymer, such as an optical property, wherein the change in the property may then determine the analyte. As used herein, the term "determination" or "determining" generally refers to the analysis of a species or signal, for example, quantitatively or qualitatively, and/or the detection of the presence or absence of the species or signals. "Determination" or "determining" may also refer to the analysis of an interaction between two or more species or signals, for example, quantitatively or qualitatively, and/or by detecting the presence or absence of the interaction.

In some embodiments, the interaction between the analyte and the binding site may comprise formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), or the like. The interaction may also comprise Van der Waals interactions. In one embodiment, the interaction comprises forming a covalent bond with an analyte. The binding site may also interact with an analyte via a binding event between pairs of biological molecules. For example, the polymeric structure may comprise an entity, such as biotin that specifically binds to a complementary entity, such as avidin or streptavidin, on a target analyte.

In some cases, the binding site may comprise a biological or a chemical molecule able to bind to another biological or chemical molecule in a medium (e.g., solution, vapor phase, solid phase). For example, the binding site may be a functional group, such as a thiol, aldehyde, ester, carboxylic acid, hydroxyl, or the like, wherein the functional group forms a bond with the analyte. In some cases, the binding site may be an electron-rich or electron-poor moiety within the polymer, wherein interaction between the analyte and the conducting polymer comprises an electrostatic interaction.

The binding site may also be capable of biologically binding an analyte via an interaction that occurs between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair.

The analyte may be a chemical or biological analyte. The term "analyte," may refer to any chemical, biochemical, or biological entity (e.g. a molecule) to be analyzed. In some cases, the polymeric structure may be selected to have high specificity for the analyte, and may be a chemical, biological, or explosives sensor, for example. In some embodiments, the analyte comprises a functional group that is capable of interacting with at least a portion of the polymeric structure. For example, the functional group may interact with the outer layer of the article by forming a bond, such as a covalent bond. In some cases, the binding site may determine changes in pH, moisture, temperature, or the like.

Figure 3:
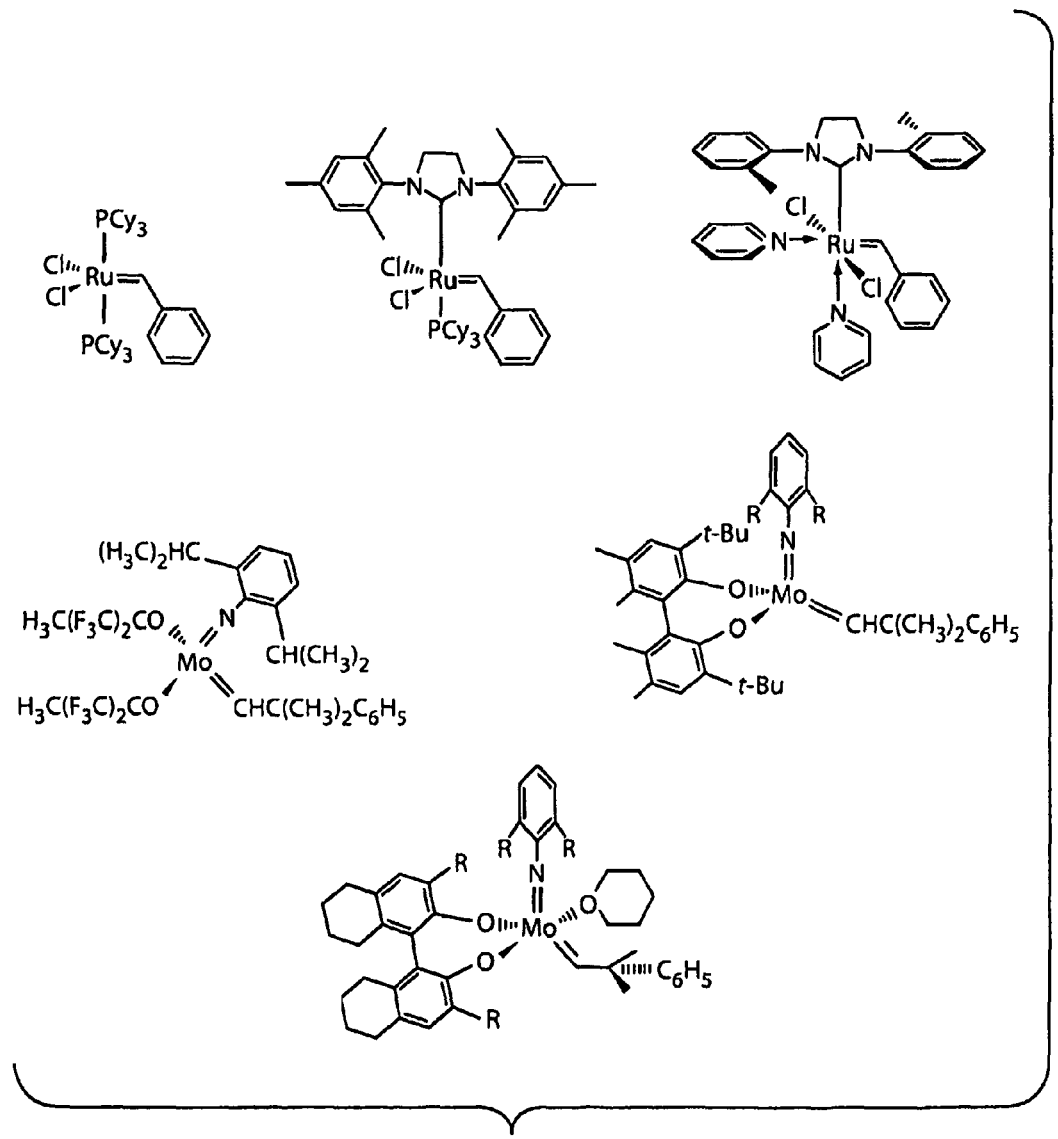
FIG. 3 shows examples of metathesis catalysts known in the art.

Metathesis catalysts suitable for use in the present invention include any species comprising a metallocarbene or metallocarbene precursor capable of reacting with an olefin or alkyne to form a four-membered ring intermediate such as a metallacyclobutane, as shown in Scheme 2, or a metallacyclobutene. The intermediate may then react further to produce a new olefin (e.g., reaction product) and a new metallocarbene, which can then be recycled through the reaction pathway. (Scheme 2) In some embodiments, the metathesis catalyst may comprise ruthenium, tungsten, or molybdenum. For example, FIG. 3 shows examples of metathesis catalysts including benzylidene-bis(tricyclohexylphosphine)dichlororuthenium (Grubbs' first generation catalyst) and benzylidene[1,3-bis(2,4,6-trimethylphenyl)-2-imidazolidinylidene]dichloro-(tricyclohexylphosphine)ruthenium (Grubbs' second generation catalyst). Other metathesis catalysts include various molybdenum-containing and tungsten catalysts, such as Schrock catalysts (e.g., tris(t-butoxy)(2,2-dimethylpropylidyne)(VI)tungsten). In some cases, the metathesis catalyst may be chiral.

Scheme 2

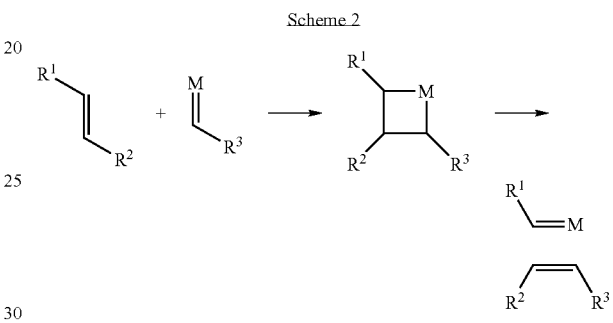

The functional group precursor may be any material comprising an olefin capable of undergoing a metathesis reaction. In some cases, the functional group precursor comprises a carbon-carbon double bond (e.g., alpha-olefin) and a functional group. In some cases, the functional group precursor comprises a carbon-carbon double bond (e.g., alpha-olefin) covalently bonded to a functional group. As described herein, the functional group may be selected to impart a particular property to, for example, the monomer or polymer. The functional group may also be selected to be stable to (e.g., chemically inert to) the metathesis catalyst or metathesis conditions. Examples of functional groups include, but are not limited to, alkyl, alkene, alkyne, heteroalkyl, cycloalkyl, heterocycloalkyl, aryl, heteroaryl, aralkyl, hydroxy, carbonyl groups, nitro, nitroso, peroxide, cyano, isocyano, amino, halogen, azo, cyanate, isocyanate, ether, acetal, imine, alkoxy, phosphine, phosphate, phosphodiester, phosphonic acid, phosphinic acid, sulfide, sulfone, sulfonic acid, sulfoxide, thiol, metal complex, substituted derivatives thereof, substituted derivatives thereof, combinations thereof, and the like. In one set of embodiments, the functional group may be a binding site for an analyte. For example, the functional group may be a Lewis acid, Lewis base, Bronsted acid, Bronsted base, hydrogen-bond donor, hydrogen-bond acceptor, or the like. In one embodiment, the functional group precursor may be 1,1,1-trifluoro-2(trifluoromethyl)-pent-4-en-2-ol.

The species, such as a monomer or polymer, may comprise groups that are capable of undergoing a metathesis reaction (e.g., an olefin). In some cases, the species (e.g., monomer, oligomer, polymer, etc.) comprises alpha-olefins. Examples of such alpha-olefins include, but are not limited to, ethylene, 1-propylene, 1-butene, 1-hexene, 1-heptene, 1-octene, 1-nonene, 1-decene, 4-methyl-1-pentene, substituted derivatives thereof, and the like. It should be understood that species of the invention may also comprise other groups capable of undergoing metathesis reactions, such as enynes. In some cases, the species may comprise terminal carbon-carbon double bonds that may react with a metathesis catalyst, as well as additional carbon-carbon double bonds which may be less reactive towards metathesis catalysts. In some cases, any additional carbon-carbon double bonds are internal (non-terminal). Those of ordinary skill in the art would be able to select other additional groups and/or reaction conditions that would be compatible with (e.g, stable to) metathesis catalysts and groups that are capable of undergoing metathesis reactions. For example, protecting group chemistry may be used in order to prevent undesired reaction between metathesis catalysts and polymerization sites within a monomer, metathesis sites (e.g., olefins, enynes) and polymerization sites within the same monomer, or metathesis sites (e.g., olefins, enynes) and other groups within a monomer, oligomer, or polymer.

In some cases, the species may be a monomer, oligomer, or polymer comprising at least two polymerization sites, i.e., at least two sites which may form bonds with other species in a polymerization reaction. Those of ordinary skill in the art would be able to select the appropriate species in order to obtain a desired polymeric product. For example, monomers comprising two hydroxyl groups may be polymerized with monomers comprising two carbonyl groups (e.g, acyl halide, carboxylic acid, etc.) to form a polyether via condensation polymerization. Likewise, monomers comprising a styrene moiety may be polymerized to form polystyrene via radical polymerization. In one embodiment, monomers comprising di-acetylene substituted aryl groups may be polymerized with monomers comprising di-halide substituted aryl groups to form poly(arylene ethynylene)s via cross-coupling polymerization. As described herein, monomers or other species of the invention may further comprise carbon-carbon double bonds that may be functionalized via metathesis chemistry.

Polymers suitable for use in the invention may comprise groups that are capable of undergoing a metathesis reaction, as described herein. As described herein, the polymers may further comprise carbon-carbon double bonds that may be functionalized via metathesis chemistry. The polymer may be homopolymers, blends of homopolymer, copolymers including random, graft and block copolymers, blends of copolymers, blends of homopolymers and copolymers, and any such systems mixed with additives such as dyes, particles, inorganic atoms and the like. In certain embodiments, the polymers may comprise mixtures of polymeric materials, or mixtures of polymeric materials and other, non-polymeric materials, and include two or more distinct domains of different composition and/or physical, chemical, or dielectric properties. In some embodiments, one or more of the distinct domains of the systems can comprise non-polymeric material or void space. In some embodiments, the polymer may be cross-linked with another polymer.

In some embodiments, at least a portion of the polymer is conjugated, wherein electron density or electronic charge is "delocalized" or may be conducted along the portion. Each p-orbital participating in conjugation can have sufficient overlap with adjacent conjugated p-orbitals. In some cases, substantial a majority of the polymer backbone is conjugated and the polymer is referred to as a "conjugated polymer." Polymers having a pi-conjugated backbone capable of conducting electronic charge are to typically referred to as "conducting polymers." Typically, atoms directly participating in the conjugation may form a plane arising from an arrangement of the p-orbitals to maximize p-orbital overlap, thus maximizing conjugation and electronic conduction.

In some cases, the polymer is a homopolymer, a random copolymer, a block copolymer, or a biological polymer. In some cases, the polymer is a conjugated polymer.

In one embodiment, the polymer is selected from the group consisting of polyarylenes, polyarylene vinylenes, polyarylene ethynylenes and ladder polymers, i.e. polymers having a backbone that can only be severed by breaking two bonds. Examples of such polymers include polythiophene, polypyrrole, polyacetylene, polyphenylene, polyiptycene, and substituted derivatives thereof.

Other examples of polymers include, but are not limited to, polyvinyl alcohol, polyvinylbutryl, polyvinylpyridyl, polyvinyl pyrrolidone, polyvinyl acetate, acrylonitrile butadiene styrene (ABS), ethylene-propylene rubbers (EPDM), EPR, chlorinated polyethylene (CPE), ethelynebisacrylamide (EBA), acrylates (e.g., alkyl acrylates, glycol acrylates, polyglycol acrylates, ethylene ethyl acrylate (EEA)), hydrogenated nitrile butadiene rubber (HNBR), natural rubber, nitrile butadiene rubber (NBR), certain fluoropolymers, silicone rubber, polyisoprene, ethylene vinyl acetate (EVA), chlorosulfonyl rubber, flourinated poly(arylene ether) (FPAE), polyether ketones, polysulfones, polyether imides, diepoxides, diisocyanates, diisothiocyanates, formaldehyde resins, amino resins, polyurethanes, unsaturated polyethers, polyglycol vinyl ethers, polyglycol divinyl ethers, copolymers thereof, polyamines (e.g., polyethylene imine) and polypropylene imine (PPI)); polyamides (e.g., polyamide (Nylon), poly($\in$-caprolactam) (Nylon 6), poly(hexamethylene adipamide) (Nylon 66)), polyimides (e.g., polyimide, polynitrile, and poly(pyromellitimide-1,4-diphenyl ether) (Kapton)); vinyl polymers (e.g., polyacrylamide, poly(2-vinyl pyridine), poly(N-vinylpyrrolidone), poly(methylcyanoacrylate), poly(ethylcyanoacrylate), poly(butylcyanoacrylate), poly(isobutylcyanoacrylate), poly(vinyl acetate), poly(vinyl alcohol), poly(vinyl chloride), poly(vinyl fluoride), poly(2-vinyl pyridine), vinyl polymer, polychlorotrifluoro ethylene, and poly(isohexylcynaoacrylate)), polyacetals, polyolefins (e.g., poly(butene-1), poly(n-pentene-2), polypropylene, polytetrafluoroethylene), polyesters (e.g., polycarbonate, polybutylene terephthalate, polyhydroxybutyrate), polyethers (poly(ethylene oxide) (PEO), poly(propylene oxide) (PPO), poly(tetramethylene oxide) (PTMO)), vinylidene polymers (e.g., polyisobutylene, poly(methyl styrene), poly(methylmethacrylate) (PMMA), poly(vinylidene chloride), and poly(vinylidene fluoride)), polyaramides (e.g., poly(imino-1,3-phenylene iminoisophthaloyl) and poly(imino-1,4-phenylene iminoterephthaloyl)), polyheteroaromatic compounds (e.g., polybenzimidazole (PSI), polybenzobisoxazole (PBO) and polybenzobisthiazole (PBT)), polyheterocyclic compounds (e.g., polypyrrole), polyurethanes, phenolic polymers (e.g., phenol-formaldehyde), polyalkynes (e.g., polyacetylene), polydienes (e.g., 1,2-polybutadiene, cis or trans-1,4-polybutadiene), polysiloxanes (e.g., poly(dimethylsiloxane) (PDMS), poly(diethylsiloxane) (PDES), polydiphenylsiloxane (PDPS), and polymethylphenylsiloxane (PMPS)), inorganic polymers (e.g., polyphosphazene, polyphosphonate, polysilanes, polysilazanes), substituted derivatives thereof, combinations thereof, and the like.

In general, the metathesis reaction may be performed by dissolving a catalytic amount of a metathesis catalyst as described herein in a solvent and adding the species and/or functional group precursor, optionally dissolved in a solvent, to the catalyst solution. Preferably, the reaction is agitated (e.g., stirred). The progress of the reaction can be monitored by standard techniques, e.g., nuclear magnetic resonance spectroscopy, thin layer chromatography, etc. In some cases, the metathesis reaction may be performed in an inert atmosphere (e.g., argon, nitrogen). In some cases, the metathesis reaction may be performed in the presence of oxygen. The metathesis reaction may be carried out in the presence of a wide variety of solvents including aqueous solvents. Examples of solvents suitable for use in a metathesis reaction include organic, protic, or aqueous solvents which are inert under the metathesis conditions, including aromatic hydrocarbons, chlorinated hydrocarbons, ethers, aliphatic hydrocarbons, alcohols, water, or mixtures thereof. Examples of specific solvents include benzene, toluene, p-xylene, methylene chloride, dichloroethane, dichlorobenzene, tetrahydrofuran, diethylether, pentane, methanol, ethanol, water, or mixtures thereof. In some cases, the metathesis reaction may be performed at a temperature of 100° C. or less, 75° C. or less, 50° C. or less, or 25° C. or less. In some cases, the metathesis reaction may be carried out under reduced pressure to remove the generated ethylene gas to shift the equilibrium towards formation of the product. Other reaction conditions may be selected to optimize the metathesis reaction, as described in *Handbook of Metathesis*, R. H. Grubbs (Ed.), Wiley-VCH, Weinheim, 2003, incorporated herein by reference.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one".

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLE 1

Compounds 61, 63, 65, and 66, Polymer 1, and Polymer 2 were synthesized and studied according to the following general methods and instrumentation. All chemicals were of reagent grade from Aldrich Chemical Co. (St. Louis, Mo.), Strem Chemicals, Inc. (Newburyport, Mass.) or Oakwood Products Inc. (West Columbia, S.C.) and used as received. All synthetic manipulations were performed under an argon atmosphere using standard Schlenk line or drybox techniques unless otherwise noted. Dichloromethane and toluene were obtained from J. T. Baker and purified by passing through a Glasscontour dry solvent system. Glassware was oven dried before use. Column chromatography was performed using Baker 40 μm silica gel. All organic extracts were dried over MgSO4 and filtered prior to removal with a rotary evaporator. Tetrakis(triphenylphosphine)palladium(0) was purchased from Strem and used as received. Grubbs' 2nd generation catalyst [1,3-bis-(2,4,6-trimethylphenyl)-2-imidazolidinylidene)dichloro(phenylmethylene)-(tri-cyclohexylphosphine)ruthenium(II)] was purchased from Aldrich. Compounds 60 and 64 were prepared according to procedures described in Kim et al., *Macromolecules* 1999, 32, 1500-1507; Kim, et al., *Nature* 2001, 411, 1030-1034; Jones, et al., *J. Chem. Soc.* 1953, 713-715; Zhou, et al., *J. Am. Chem. Soc.*, 1995, 117, 12593; and Yang, et al., *J. Am. Chem. Soc.* 1998, 120, 11864-11873. Compound 68 was purchased from Nomadics Inc. (Stillwater, Okla.).

$^1$H NMR, $^{13}$C NMR, and $^{19}$F NMR spectra were obtained on Varian Mercury (300 MHz), Bruker Avance-400 (400 MHz), and Varian Inova (500 MHz) instruments. NMR chemical shifts are referenced to CHC$^{13}$/TMS (7.27 ppm for $^1$H, 77.23 ppm for $^{13}$C). For $^{19}$F NMR spectra, trichlorofluoromethane was used as an external standard (0 ppm) and upfield shifts are reported as negative values. Mass spectra (MS) were obtained at the MIT Department of Chemistry Instrumentation Facility (DCIF) using a peak-matching protocol to determine the mass and error range of the molecular ion.

All polymer solutions were filtered through 0.45 micron syringe filters prior to use. Polymer molecular weights were determined at room temperature on a HP series 1100 GPC system in THE at 1.0 mL/min (1 mg/mL sample concentrations) equipped with a diode array detector (254 nm and 450 nm) and a refractive index detector. Polymer molecular weights are reported relative to polystyrene standards. Melting points were measured with a Meltemp II apparatus and are reported uncorrected.

EXAMPLE 2

Compound 61 was synthesized according to the following method. Into a 25 mL roundbottom flask, fitted with a refluxing condenser and a magnetic stirring bar, were added 0.90 g (1.8 mmol) of 1, 0.87 g (5.8 mmol) of 5-bromo-1-pentene, 0.30 g (2.2 mmol) of potassium carbonate, 0.12 g (0.7 mmol) of potassium iodide, and 20 mL of 2-butanone. The suspension was heated to reflux for 18 hours. After cooling to room temperature, water (50 mL) and ethyl ether (50 mL) were added. The organic layer was extracted into ethyl ether (3×50 mL), washed with water (3×50 mL) and dried to yield a green oil. The crude product was purified by column chromatography (0-10% CH$_2$Cl$_2$ in hexanes) to yield 0.78 g (76%) of a colorless crystalline solid. mp: 293° C. $^1$H NMR (300 MHz, CDCl$_3$) δ: 7.18 (s, 2H), 5.80-5.87 (m, 1H), 5.05-5.14 (m, 1H), 5.00-5.05 (m, 1H), 3.94 (dd, 4H, J=6, 12 Hz), 2.25-2.35 (m, 2H), 1.85-1.95 (m, 2H), 1.75-1.85 (m, 2H), 1.43-1.55 (m, 4H), 1.23-1.44 (m, 10H), 0.85-0.92 (m, 3H). $^{13}$C NMR (75 MHz, CDCl$_3$) δ: 153.1, 152.9, 137.9, 122.9, 122.8, 115.6, 86.5, 86.4, 70.5, 69.6, 32.1, 30.3, 29.8, 29.7, 29.5, 29.4, 29.3, 28.5, 26.2, 22.9, 14.4. MS (EI): calcd for C$_{21}$H$_{32}$I$_2$O$_2$ (M$^+$), 570.0486; found 570.0460.

EXAMPLE 3

Compound 63 was synthesized according to the following method. Into a 25 mL Schlenk tube with a magnetic stirring bar were added 0.10 g (0.2 mmol) of compound 25, and 0.01 g (0.01 mmol) of Grubbs' 2nd generation catalyst. A solution of 1,1,1-trifluoro-2(trifluoromethyl)-pent-4-en-2-ol (compound 62) 0.37 g (1.8 mmol) in 0.5 mL, CH$_2$Cl$_2$ was added and the reaction mixture was heated to 65° C. for 18 hours. After cooling to room temperature, the solvent was removed and the crude product was purified by column chromatography (0-10% ethyl acetate in hexanes) to yield 0.09 g (67%) of a colorless solid. mp: 51-52° C. $^1$H NMR (500 MHz, CDCl$_3$) δ: 7.18 (m, 2H), 5.82-5.94 (m, 1H), 5.48-5.56 (m, 1H), 3.94 (m, 4H), 2.94 (s, 1H), 2.70 (d, 2H, J=8 Hz), 2.34-2.42 (dd, 2H, J=7, 14), 1.88-1.96 (m, 2H), 1.78-1.84 (m, 2H), 1.46-1.54 (m, 2H), 1.25-1.40 (m, 12H), 0.85-0.92 (m, 3H). $^{13}$C NMR (125 MHz, CDCl$_3$) δ: 153.3, 152.7, 139.7, 123.1, 122.9, 120.2, 86.5, 86.4, 70.5, 69.6, 33.8, 32.1, 29.8, 29.7, 29.6, 29.5, 29.4, 29.3, 28.7, 26.2, 24.1, 22.9, 14.3. $^{19}$F NMR (282 MHz, CDCl$_3$): –76.9, –77.1 (two isomers). MS (EI): calcd for C$_{25}$H$_{34}$F$_6$I$_2$O$_3$ (M$^+$), 750.0496; found 750.0478.

EXAMPLE 4

Compound 65 was synthesized according to the following method. Into a 25 mL roundbottom flask, fitted with a refluxing condenser and a magnetic stirring bar, were added 0.20 g (0.6 mmol) of 5, 0.50 g (3.4 mmol) of 5-bromo-1-pentene, 0.20 g (1.4 mmol) of potassium carbonate, 0.08 g (0.5 mmol) of potassium iodide, and 6 mL, of 2-butanone. The suspension was heated to reflux for 18 hours. After cooling to room temperature, water (50 mL) and ethyl ether (50 mL) were added. The organic layer was extracted into ethyl ether (3×50 mL), washed with water (3×50 mL) and dried to yield a green oil. The crude product was purified by column chromatography (0-5% ethyl acetate in hexanes) to yield 0.23 g (85%) of colorless crystals. mp: 41-42° C. $^1$H NMR (300 MHz, CDCl$_3$) δ: S 7.18 (s, 2H), 5.80-5.95 (m, 2H), 5.05-5.14 (m, 2H), 4.98-5.05 (m, 2H), 3.95 (t, 4H, J=6), 2.26-2.37 (dd, 4H, J=7, 14), 1.86-1.98 (m, 4H). $^{13}$C NMR (75 MHz, CDCl$_3$) δ: 152.9, 137.8, 122.9, 115.6, 86.5, 69.5, 30.3, 28.5. MS (ESI): calcd for C$_{16}$H$_{20}$I$_2$O$_2$ (M+Na)$^+$, 520.9445; found 520.9455.

EXAMPLE 5

Compound 66 was synthesized according to the following method. Into a 50 mL Schlenk tube with a magnetic stirring bar were added 0.50 g (1.0 mmol) of compound 29, and 0.08 g (0.1 mmol) of Grubbs' 2nd generation catalyst. A solution of 1,1,1-trifluoro-2(trifluoromethyl)-pent-4-en-2-ol (compound 62) 3.13 g (15.0 mmol) in 2.5 mL, CH$_2$Cl$_2$ was added and the reaction mixture was heated to 65° C. for 48 hours. After cooling to room temperature, the solvent was removed and the crude product was purified by column chromatography (0-33% ethyl acetate in hexanes) to yield an oily paste. Trituration with hexanes afforded 0.1 g (12%, first crop) of colorless crystals. mp: 125-126° C. $^1$H NMR (400 MHz, CDCl$_3$) δ: 7.17 (s, 2H), 5.80-5.88 (m, 2H), 5.48-5.55 (m, 2H), 3.96 (t, 4H, J=6 Hz), 2.94 (s, 2H), 2.69-2.71 (d, 4H, J=8 Hz), 2.34-2.42 (dd, 4H, J=7, 14), 1.90-1.94 (m, 4H). $^{13}$C NMR (100 MHz, CDCl$_3$) δ: 153.0, 139.7, 123.1, 120.3, 86.5, 69.5, 33.7, 29.4, 28.7. $^{19}$F NMR (282 MHz, CDCl$_3$) δ: –76.9. MS (ESI): calcd for C$_{24}$H$_{24}$F$_{12}$I$_2$O$_4$ (M+Na)$^+$, 880.9465; found 880.9459.

EXAMPLE 6

Figure 6A:
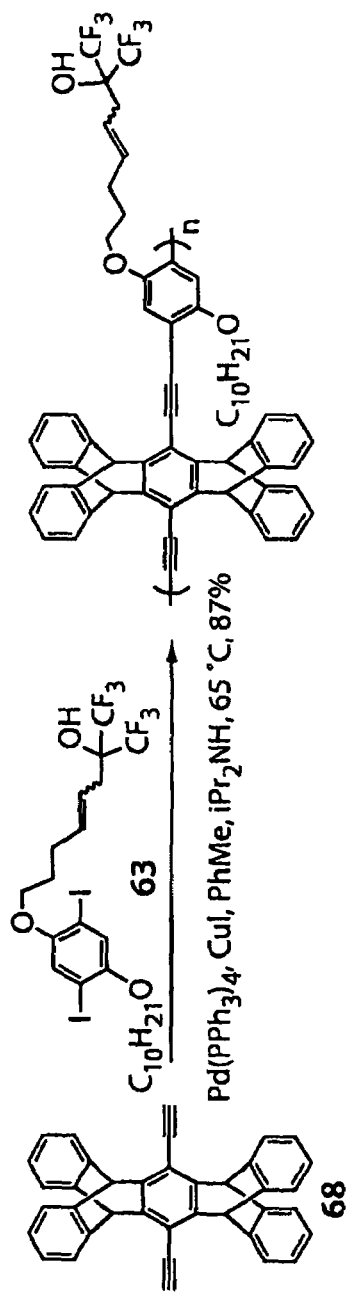
FIGS. 6A-B show a schematic syntheses of polymers containing hexafluoroisopropanol groups.
Figure 6B:
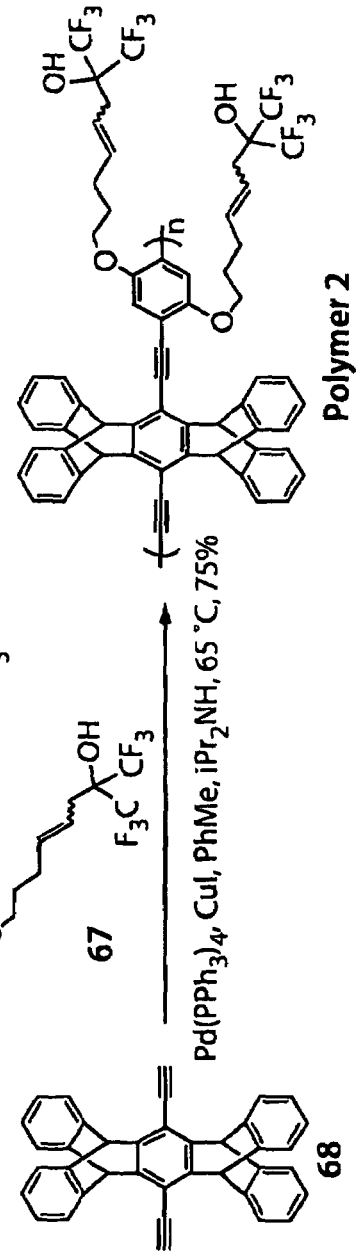

A general procedure for the synthesis of Polymer 1 and Polymer 2 is illustrated by the synthesis of Polymer 1, as described below. Polymer 2 was prepared in a similar manner from compounds 67 and 68. FIG. 6A shows the synthesis of Polymer 1 and FIG. 6B shows the synthesis of Polymer 2. All polymers were characterized by $^1$H and $^{19}$F NMR spectroscopy, gel permeation chromatography (GPC), as well as UV-VIS, and fluorescence spectroscopy.

Into a 25 mL Schlenk tube with a magnetic stirring bar were added compound 63 (15 mg, 0.02 mmol), compound 68 (9.7 mg, 0.02 mmol), and small amounts of copper iodide (<1 mg), and Pd(PPh$_3$)$_4$ (<1 mg). A deoxygenated solution of 3:2

(v/v) 4 Solvents were deoxygenated by vigorous argon bubbling for 20 minutes. toluene/diisopropylamine (0.750 mL) was then added. The tube was sealed and heated to 65° C. for 72 hours. After cooling to room temperature, the reaction mixture was precipitated by slow addition to 20 mL of methanol. The precipitate was isolated by centrifugation and decantation of the supernatant. The precipitate was washed with several 20 mL portions of methanol to remove any short oligomers. The material was dried under vacuum to yield a yellow solid (17 mg, 87%).

Polymer 1: GPC (THF): $M_n$=17K, $M_w$=37K. $^1$H NMR (300 MHz, CDCl$_3$) δ: 7.40-7.55 (aromatic C—H), 6.96-7.10 (aromatic C—H), 5.90-6.20 (iptycene bridgehead C—H), 5.60-5.78 (olefinic C—H), 5.30-5.45 (olefinic C—H), 4.38-4.55 (aliphatic C—H), 4.15-4.32 (aliphatic C—H), 2.65-3.05 (aliphatic C—H), 2.43-2.58 (aliphatic C—H), 2.18-2.32 (aliphatic C—H), 1.68-1.80 (aliphatic C—H), 1.35-1.68 (aliphatic C—H), 1.10-1.35 (aliphatic C—H), 0.78-0.95 (aliphatic C—H). 8. 1917 NMR (282 MHz, CDCl3): δ —76.8, −77.0. (two isomers)

Polymer 2: (75%) GPC (THF): $M_n$=26K, $M_w$=60K. $^1$H NMR (300 MHz, CDCl$_3$) δ: 7.44-7.52 (aromatic C—H), 6.96-7.09 (aromatic C—H), 6.02-6.14 (iptycene bridgehead C—H), 5.62-5.78 (olefinic C—H), 5.28-5.42 (olefinic C—H), 4.42-4.52 (aliphatic C—H), 2.88-2.98 (aliphatic C—H), 2.75-2.80 (aliphatic C—H), 2.44-2.56 (aliphatic C—H), 2.18-2.30 (aliphatic C—H). 1917 NMR (282 MHz, CDCl3): δ −76.9, −77.0 (two isomers).

What is claimed:

1. A method for synthesizing a polymer containing a desired functional group, comprising:
providing a species comprising a carbon-carbon double bond;
performing a metathesis reaction between the species and a functional group precursor to form a covalent bond therebetween, thereby forming a functionalized species; and
polymerizing the functionalized species, with or without other non- or differently-functionalized species, to form a conjugated polymer comprising the functional group.

2. A method as in claim 1, wherein performing the metathesis reaction comprises exposing the species and the functional group precursor to a metathesis catalyst comprising ruthenium, molybdenum, or tungsten.

3. A method as in claim 1, wherein the metathesis reaction is a cross-metathesis, a ring-closing metathesis, or a ring-opening metathesis reaction.

4. A method as in claim 1, wherein polymerizing the functionalized species comprises cationic polymerization, anionic polymerization, radical polymerization, condensation polymerization, Wittig polymerization, ring-opening polymerization, cross-coupling polymerization, addition polymerization, or chain polymerization.

5. A method as in claim 1, wherein the functional group precursor comprises a carbon-carbon double bond and the functional group.

6. A method as in claim 1, wherein the functional group precursor comprises alkyl, alkene, alkyne, heteroalkyl, cycloalkyl, heterocycloalkyl, aryl, heteroaryl, aralkyl, hydroxy, carbonyl groups, nitro, nitroso, peroxide, cyano, isocyano, amino, halogen, azo, cyanate, isocyanate, ether, acetal, imine, alkoxy, phosphine, phosphate, phosphodiester, phosphonic acid, phosphinic acid, sulfide, sulfone, sulfonic acid, sulfoxide, thiol, metal complex, substituted derivatives thereof, or combinations thereof.

7. A method as in claim 1, wherein the polymer is a homopolymer, a random copolymer, a block co-polymer, or a biological polymer.

8. A method as in claim 1, wherein the polymer comprises a pendant group comprising the functional group.

9. A method as in claim 1, wherein the metathesis reaction is performed at a temperature of 100° C. or less.

10. A method as in claim 1, wherein the metathesis reaction is performed at a temperature of 75° C. or less.

11. A method as in claim 1, wherein the metathesis reaction is performed at a temperature of 50° C. or less.

12. A method as in claim 1, wherein the metathesis reaction is performed at a temperature of 25° C. or less.

13. A method for synthesizing a polymer containing a desired functional group, comprising:
providing a polymer comprising at least one carbon-carbon double bond; and
performing a metathesis reaction between the polymer and a functional group precursor such that a covalent bond is formed therebetween, thereby forming a conjugated polymer comprising the functional group.

14. A method as in claim 13, wherein performing the metathesis reaction comprises exposing the polymer and the functional group precursor to a catalyst comprising ruthenium, molybdenum, or tungsten.

15. A method as in claim 13, wherein the metathesis reaction is a cross-metathesis, a ring-closing metathesis, or a ring-opening metathesis reaction.

16. A method as in claim 13, wherein the polymer comprising at least one carbon-carbon double bond comprises a pendant group comprising the carbon-carbon double bond.

17. A method as in claim 13, wherein the functional group precursor comprises a carbon-carbon double bond and the functional group.

18. A method as in claim 13, wherein the functional group precursor comprises alkyl, alkene, alkyne, heteroalkyl, cycloalkyl, heterocycloalkyl, aryl, heteroaryl, aralkyl, hydroxy, carbonyl groups, nitro, nitroso, peroxide, cyano, isocyano, amino, halogen, azo, cyanate, isocyanate, ether, acetal, imine, alkoxy, phosphine, phosphate, phosphodiester, phosphonic acid, phosphinic acid, sulfide, sulfone, sulfonic acid, sulfoxide, thiol, metal complex, substituted derivatives thereof, or combinations thereof.

19. A method as in claim 13, wherein the polymer is a homopolymer, a random copolymer, a block co-polymer, or a biological polymer.

20. A method as in claim 13, wherein the metathesis reaction is performed at a temperature of 100° C. or less.

21. A method as in claim 13, wherein the metathesis reaction is performed at a temperature of 75° C. or less.

22. A method as in claim 13, wherein the metathesis reaction is performed at a temperature of 50° C. or less.

23. A method as in claim 13, wherein the metathesis reaction is performed at a temperature of 25° C. or less.

24. A method for synthesizing a polymer containing a desired functional group, comprising:
providing a polymer comprising at least one carbon-carbon double bond; and
performing a metathesis reaction between the polymer and a functional group precursor such that a covalent bond is formed therebetween, thereby forming a conjugated polymer comprising a pendant group comprising the functional group.

25. A method as in claim 24, wherein performing the metathesis reaction comprises exposing the polymer and the functional group precursor to a catalyst comprising ruthenium, molybdenum, or tungsten.

26. A method as in claim 24, wherein the metathesis reaction is a cross-metathesis, a ring-closing metathesis, or a ring-opening metathesis reaction.

27. A method as in claim 24, wherein the polymer comprising at least one carbon-carbon double bond comprises a pendant group comprising the carbon-carbon double bond.

28. A method as in claim 24, wherein the functional group precursor comprises a carbon-carbon double bond and the functional group.

29. A method as in claim 24, wherein the functional group precursor comprises alkyl, alkene, alkyne, heteroalkyl, cycloalkyl, heterocycloalkyl, aryl, heteroaryl, aralkyl, hydroxy, carbonyl groups, nitro, nitroso, peroxide, cyano, isocyano, amino, halogen, azo, cyanate, isocyanate, ether, acetal, imine, alkoxy, phosphine, phosphate, phosphodiester, phosphonic acid, phosphinic acid, sulfide, sulfone, sulfonic acid, sulfoxide, thiol, metal complex, substituted derivatives thereof, or combinations thereof.

30. A method as in claim 24, wherein the polymer is a homopolymer, a random copolymer, a block co-polymer, or a biological polymer.

31. A method as in claim 24, wherein the metathesis reaction is performed at a temperature of 100° C. or less.

32. A method as in claim 24, wherein the metathesis reaction is performed at a temperature of 75° C. or less.

33. A method as in claim 24, wherein the metathesis reaction is performed at a temperature of 50° C. or less.

34. A method as in claim 24, wherein the metathesis reaction is performed at a temperature of 25° C. or less.

35. A method for synthesizing a polymer containing a desired functional group, comprising:
providing a polymer comprising at least one pendant group comprising a carbon-carbon double bond; and
performing a metathesis reaction between the polymer and a functional group precursor such that a covalent bond is formed therebetween, thereby forming a conjugated polymer comprising the functional group.

36. A method as in claim 35, wherein performing the metathesis reaction comprises exposing the polymer and the functional group precursor to a catalyst comprising ruthenium, molybdenum, or tungsten.

37. A method as in claim 35, wherein the metathesis reaction is a cross-metathesis, a ring-closing metathesis, or a ring-opening metathesis reaction.

38. A method as in claim 35, wherein the functional group precursor comprises a carbon-carbon double bond and the functional group.

39. A method as in claim 35, wherein the functional group precursor comprises alkyl, alkene, alkyne, heteroalkyl, cycloalkyl, heterocycloalkyl, aryl, heteroaryl, aralkyl, hydroxy, carbonyl groups, nitro, nitroso, peroxide, cyano, isocyano, amino, halogen, azo, cyanate, isocyanate, ether, acetal, imine, alkoxy, phosphine, phosphate, phosphodiester, phosphonic acid, phosphinic acid, sulfide, sulfone, sulfonic acid, sulfoxide, thiol, metal complex, substituted derivatives thereof, or combinations thereof.

40. A method as in claim 35, wherein the polymer is a homopolymer, a random copolymer, a block co-polymer, or a biological polymer.

41. A method as in claim 35, wherein the polymer comprises a pendant group comprising the functional group.

42. A method as in claim 35, wherein the metathesis reaction is performed at a temperature of 100° C. or less.

43. A method as in claim 35, wherein the metathesis reaction is performed at a temperature of 75° C. or less.

44. A method as in claim 35, wherein the metathesis reaction is performed at a temperature of 50° C. or less.

45. A method as in claim 35, wherein the metathesis reaction is performed at a temperature of 25° C. or less.

* * * * *